United States Patent
Luke et al.

(10) Patent No.: US 6,770,627 B1
(45) Date of Patent: Aug. 3, 2004

(54) PIPERIZINE-4-PHENYL DERIVATIVES AS INHIBITORS OF THE INTERACTION BETWEEN MDM2 AND P 53

(75) Inventors: Richard Wa Luke, Macclesfield (GB); Philip J. Jewsbury, Macclesfield (GB); Ronald Cotton, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/786,702

(22) PCT Filed: Sep. 7, 1999

(86) PCT No.: PCT/GB99/02957

§ 371 (c)(1),
(2), (4) Date: Mar. 7, 2001

(87) PCT Pub. No.: WO00/15657

PCT Pub. Date: Mar. 23, 2000

(30) Foreign Application Priority Data

Sep. 12, 1998 (GB) .............................. 9819860

(51) Int. Cl.[7] ..................... A61K 31/495; A61K 31/496; A61K 38/06; C07D 295/185; C07K 5/08
(52) U.S. Cl. ...................... 514/18; 514/19; 514/252.13; 514/254.09; 514/255.01; 530/331; 544/359; 544/373; 544/386; 544/391
(58) Field of Search ....................... 514/18, 19, 252.13, 514/254.09, 255.01; 530/331; 544/359, 373, 386, 391

(56) References Cited

U.S. PATENT DOCUMENTS

| | | | |
|---|---|---|---|
| 4,618,708 A | 10/1986 | Roques et al. | 560/312 |
| 4,738,803 A | 4/1988 | Roques et al. | 560/312 |
| 5,367,081 A | 11/1994 | Ikawa et al. | 546/316 |
| 5,411,860 A | 5/1995 | Vogelstein et al. | 435/6 |
| 5,550,023 A | 8/1996 | Kinzler et al. | 435/7.1 |
| 5,596,000 A | 1/1997 | Esser et al. | 514/312 |
| 5,607,936 A | 3/1997 | Chiang et al. | 514/255 |
| 5,700,827 A | 12/1997 | Schnorrenberg et al. | 514/414 |
| 5,708,136 A | 1/1998 | Burrell et al. | 530/324 |
| 5,712,273 A | 1/1998 | Schnorrenberg et al. | 514/218 |
| 5,747,535 A | 5/1998 | Oh et al. | 514/507 |
| 5,756,455 A | 5/1998 | Kinzler et al. | 514/12 |
| 5,770,377 A | 6/1998 | Picksley et al. | 435/7.1 |
| 5,885,999 A | 3/1999 | Elliott et al. | 514/258 |
| 6,057,290 A | 5/2000 | Fukiage et al. | 514/12 |
| 6,344,449 B1 | 2/2002 | Rudolf et al. | 514/217.05 |

FOREIGN PATENT DOCUMENTS

| | | |
|---|---|---|
| DE | 423858 | 6/1994 |
| EP | 0 771 565 A2 * | 5/1997 |
| JP | 3-127732 * | 5/1991 |
| JP | 05294915 | 11/1993 |
| WO | WO 94/07496 | 4/1994 |
| WO | WO 95/34311 | 12/1995 |
| WO | WO 97/09343 | 3/1997 |
| WO | WO 97/37983 | 10/1997 |
| WO | WO 98/01467 | 1/1998 |
| WO | WO 98/25617 | 6/1998 |

OTHER PUBLICATIONS

Chemical Abstracts, vol. 116, No.13, Mar. 1992 Columbus, Ohio, US; abstract No. 128656Z, Furuta Takuya et al.: "Preparation of Indole Derivatives as Vasopressin Antagonists" p. 863; col. 1; XP002125251 abstract.

Chemical Abstracts 13th Collective Index; Chemical Substances (Azau . . . –Benzamide, Tetrae . . . ), vol. 116–125, 1992–1996, p. 1647 XP002125250 Columbus, Ohio, US, col. 2, line 60–line 64 & JP 03 127732 A (Otsuka Pharmaceutical) May 30, 1991.

Barakat, K.J. et al. Synthesis and Biological Activities of Pheayl Piperazinc–Based Peptidormimetic Growth Hormone Secretagogues. Bioorg. Med. Chem. Lett. 8, 1431–1436 (1998).

Sakamoto, H. et al. Chymotrypsin Inhibition by Dipeptide Esters, Phenylpiperididde and Phenylpiperazides Pept. Chem, 27, 375–378 (1990).

Sakamoto, H. et al. Dipeptide Side Chain–Side Chain Hydrophobic Interactions as Confromational Core for Chymotrypsin Inhibition. Bull. Chem. Soc. Jpn 64, 2519–2523 (1991).

* cited by examiner

Primary Examiner—Jeffrey E. Russel
(74) Attorney, Agent, or Firm—Ropes & Gray LLP

(57) ABSTRACT

A compound of formula (1), wherein: $R_5$ is hydrogen, $C_{1-4}$alkyl, $R_6CH_2$— or $R_6C(O)$—; $R_6$ is aryl, heteroaryl, heterocyclyl, amino$C_{3-6}$alkyl, N-($C_{1-4}$alkyl)amino$C_{3-6}$alkyl, NN-(di$C_{1-4}$alkyl)amino$C_{3-6}$alkyl, or $R_7$; wherein the aryl, heteroaryl or heterocyclyl rings may be optionally substituted with up to three substituents independently selected from nitro, $C_{1-4}$alkyl, $C_{1-4}$alkoxy, halo, ($C_{1-4}$alkyl)sulfanyl, $C_{1-4}$alkoxycarbonyl, N-($C_{1-4}$alkyl)carbamoyl, NN-(di$C_{1-4}$ alkyl)carbamoyl, N-($C_{1-4}$alkyl)amino or NN-(di$C_{1-4}$alkyl) amino; wherein R7 is either a group or formula (2) or formula (3); and wherein $L_1$, $L_2$, $L_3$, $L_4$, $R_1$, $R_2$, $R_3$, $R_4$, $R_8$, $R_9$, $R_{10}$, $R_{11}$, $R_{12}$, $R_{13}$, $A_1$, n, p, q, r and s are as defined herein. The compounds of formula (1) inhibit the interactions between MDM2 and p53 and may be useful in the treatment of cancers.

15 Claims, No Drawings

SEQUENCE LISTING

<160> NUMBER OF SEQ ID NOS: 1

<210> SEQ ID NO 1
<211> LENGTH: 21
<212> TYPE: DNA
<213> ORGANISM: Artificial Sequence
<220> FEATURE:
<223> OTHER INFORMATION: expression vector

<400> SEQUENCE: 1
ctggttccgc gtggatccat g                                         21

PIPERIZINE-4-PHENYL DERIVATIVES AS INHIBITORS OF THE INTERACTION BETWEEN MDM2 AND P 53

This application is the national phase of international application PCT/GB99/02957 filed Sep. 7, 1999 which designated the U.S.

This invention relates to compounds which inhibit the interaction between MDM2 and the tumour suppressor protein, p53. This invention also relates to processes for the manufacture of MDM2/p53 interaction inhibitors and pharmaceutically acceptable salts, prodrugs or solvates thereof, to novel pharmaceutical compositions containing them and to the use of the compounds as probes of MDM2 and p53 function.

p53 is a transcription factor which plays a pivotal role in the regulation of the balance between cell proliferation and cell growth arrest/apoptosis. Under normal conditions the half life of p53 is very short and consequently the level of p53 in cells is low. However, in response to cellular DNA damage or cellular stress, levels of p53 increase. This increase in p53 levels leads to the activation of the transcription of a number of genes which induces the cell to either growth arrest or to undergo the processes of apoptosis. Thus the function of p53 is to prevent the proliferation of transformed cells and thus protect the organism from the development of cancer (for a review see Levine 1997, Cell 88, 323–331).

MDM2 is a key negative regulator of p53 function, which binds to the amino terminal transactivation domain of p53. MDM2 both inhibits the ability of p53 to activate transcription and targets p53 for proteolytic degradation, thus maintaining the low levels of p53 under normal conditions. MDM2 may also have separate functions in addition to inhibition of p53. For example, MDM2 also binds another tumour suppressor protein, the retinoblastoma gene product, and inhibits its ability to activate transcription. For reviews of MDM2 function see: Piette et al (1997) Oncogene 15, 1001–1010; Lane and Hall (1997) TIBS 22, 372–374; Lozano and de Oca Luna (1998) Biochim Biophys Acta 1377, M55–M59.

MDM2 is a cellular proto-oncogene. Overexpression of MDM2 has been observed in a range of cancers see Momand and Zambetti (1997) J. Cell. Biochem 64, 343–352. The mechanism by which MDM2 amplification promotes tumourigenesis is at least in part related to its interaction with p53. In cells over-expressing MDM2 the protective function of p53 is blocked and thus cells are unable to respond to DNA damage or cellular stress by increasing p53 levels, leading to cell growth arrest and/or apoptosis. Thus after DNA damage and/or cellular stress cells over-expressing MDM2 are free to continue to proliferate and assume a tumourigenic phenotype. Under these conditions disruption of the interaction of p53 and MDM2 would release the p53 and thus allow the normal signals of growth arrest and/or apoptosis to function. Thus disruption of the interaction of MDM2 and p53 offers an approach for therapeutic intervention in cancer.

A few patent applications have been published which describe peptide inhibitors of the interaction of p53 and MDM2, see: International Patent Application, WO9602642, University of Dundee; International Patent Application WO 9801467, Novartis & Cancer Research Campaign Technology Ltd.; and International Patent Application WO 9709343.

We have discovered a novel class of small molecule compounds which inhibit the interaction of MDM2 and p53. These compounds are useful as probes of MDM2 and p53 function and may be useful as agents for the treatment of cancer.

According to the invention there is provided a compound of formula (1):

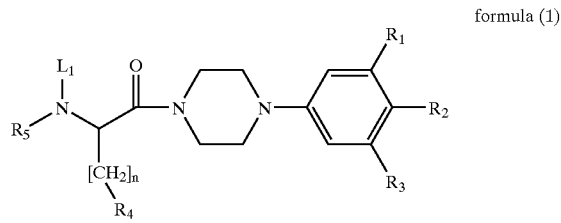

formula (1)

wherein:

$L_1$ is hydrogen or methyl;

$R_1$ and $R_2$ and $R_3$ are each independently hydrogen, halo, nitro, cyano, carbamoyl, N-($C_{1-4}$alkyl)carbamoyl, NN-(di$C_{1-4}$alkyl)carbamoyl or $C_{1-4}$alkoxycarbonyl;

$R_4$ is indole, N-($C_{1-4}$ alkyl) indole, $C_{5-7}$carbocyclic ring or aryl, any of which can be optionally substituted on ring carbon atoms with up to three substituents each independently selected from halo, $C_{1-4}$alkyl, or $C_{1-4}$alkoxy;

$R_5$ is hydrogen, $C_{1-4}$alkyl, $R_6CH_2$— or $R_6C(O)$—;

$R_6$ is aryl, heteroaryl, heterocyclyl, amino$C_{3-6}$alkyl, N($C_{1-4}$alkyl)amino$C_{3-6}$alkyl, NN-(di$C_{1-4}$alkyl)amino$C_{3-6}$alkyl, or $R_7$; wherein the aryl, heteroaryl or heterocyclyl rings may be optionally substituted with up to three substituents independently selected from nitro, $C_{1-4}$alkyl, $C_{1-4}$alkoxy, halo, ($C_{1-4}$alkyl)sulfanyl, $C_{1-4}$ alkoxycarbonyl, N-($C_{1-4}$ alkyl)carbamoyl, NN-(di$C_{1-4}$ alkyl)carbamoyl, N-($C_{1-4}$ alkyl)amino or NN-(di$C_{1-4}$ alkyl)amino;

wherein $R_7$ is either a group of formula (2) of formula (3):

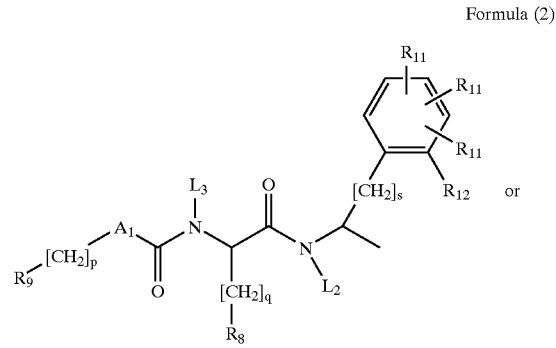

Formula (2)

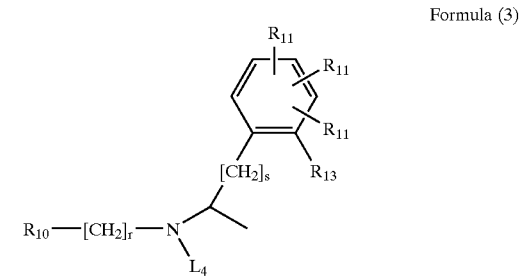

Formula (3)

wherein:

$L_2$, $L_3$ and $L_4$ are each independently hydrogen or methyl;

$R_8$ is amino, guanadino, imidazolo, any of which can be mono or di-N-substituted with $C_{1-4}$alkyl;

$A_1$ is oxygen or a direct bond;

$R_9$ is a $C_{5-8}$ membered mono-carbocyclic ring, a $C_{6-10}$ membered bi-carbocyclic ring, $C_{8-12}$ membered tri-carbocyclic ring, $C_{5-7}$alkyl or aryl, any of which can be optionally mono, bi or tri substituted by $C_{1-4}$ alkyl, $R_{10}$ is $C_{1-6}$alkyl or a $C_{3-8}$mono-carbocyclic ring;

$R_{11}$ is hydrogen, halo, $C_{1-4}$alkyl, or $C_{1-4}$alkoxy;

$R_{12}$ is hydrogen or methyl or ethyl or $R_{12}$ together with $L_2$ forms a $C_{5-7}$ nitrogen-containing heterocyclic ring;

$R_{13}$ is hydrogen or methyl ethyl or $R_{13}$ together with $L_4$ forms a $C_{5-7}$ nitrogen-containing heterocyclic ring;

n is 0, 1 or 2;

p is 0, 1 or 2;

q is an integer from 1 to 6 r is 0, 1 or 2;

s is 0, 1 or 2;

provided that when $R_6$ is aryl, heteroaryl, heterocyclyl amino$C_{3-6}$alkyl, N-($C_{1-4}$alkyl)amino$C_{3-6}$alkyl or NN-(di$C_{1-4}$alkyl)amino$C_{3-6}$alkyl then $R_6$ is other than $R_6CH_2$—; and when $R_1$ is hydrogen, $R_2$ is hydrogen, $R_3$ is hydrogen, $L_1$ is hydrogen, n is 1, $R_4$ is phenyl, $R_5$ is $R_6C(O)$—, then $R_6$ cannot be 2-methyl-4-aminobutyl, or a pharmaceutically acceptable salt, prodrug or solvate thereof.

In this specification the generic term "alkyl" includes both straight-chain and branched-chain alkyl groups. However references to individual alkyl groups such as "propyl" are specific for the straight-chain version only and references to individual branched-chain alkyl groups such as "isopropyl" are specific for the branched-chain version only. An analogous convention applies to other generic terms.

The term "aryl" refers to phenyl or naphthyl.

The term "heteroaryl" refers to a 5–10 membered aromatic mono or bicyclic ring containing up to 5 heteroatoms selected from nitrogen, oxygen or sulphur. Examples of 5- or 6-membered heteroaryl ring systems include imidazole, triazole, pyrazine, pyrimidine, pyridazine, pyridine, isoxazole, oxazole, isothiazole, thiazole, furan, pyrazole, 1,2,3-thiadiazole and thiophene. A 9 or 10 membered bicyclic heteroaryl ring system is an aromatic bicyclic ring system comprising a 6-membered ring fused to either a 5 membered ring or another 6 membered ring. Examples of 5/6 and 6/6 bicyclic ring systems include benzofuran, benzimidazole, benzthiophene, benzthiazole, benzisothiazole, benzoxazole, benzisoxazole, pyridoimidazole, pyrimidoimidazole, quinoline, isoquinoline, quinoxaline, quinazoline, phthalazine, cinnoline, 4-oxo-4H-1-benzopyran and naphthyridine.

The term "heterocyclyl" refers to a 5–10 membered non-aromatic mono or bicyclic ring containing up to 5 heteroatoms selected from nitrogen, oxygen or sulphur. Examples of 'heterocyclyl' include pyrrolinyl, pyrrolidinyl, morpholinyl, piperidinyl, piperazinyl, dihydropyridinyl and dihydropyrimidinyl The term "carbocyclic ring" refers to a totally saturated or partially saturated mono, bi or tri cyclic carbon ring. Examples of carbocyclic rings are cyclopentyl, cyclohexyl, cyclopentyl, bicyclo-octane or adamantyl.

The term "halo" refers to fluorine, chlorine, bromine or iodine.

The term carbamoyl refers to —C(O)NH$_2$.

The term "warm-blooded animal" includes human.

Examples of $C_{1-4}$alkyl include methyl, ethyl, propyl, isopropyl, sec-butyl and tert-butyl; examples of $C_{1-4}$alkoxy include methoxy, ethoxy and propoxy; examples of $C_{1-4}$alkanoyl include formyl, acetyl and propionyl; examples of $C_{1-4}$alkylamino include methylamino, ethylamino, propylamino, isopropylamino, sec-butylamino and tert-butylamino; examples of di-($C_{1-4}$alkyl)amino include di-methylamino, di-ethylamino and N-ethyl-N-methylamino; examples of N-($C_{1-4}$alkyl)amino$C_{1-4}$alkyl include N-methyl-aminomethyl and N-ethyl-aminoethyl, and examples of NN-di($C_{1-4}$alkyl)amino$C_{1-4}$alkyl include: NN-dimethyl-aminomethyl and N-methyl-N-ethyl aminomethyl.

Examples of suitable values for $R_1$, $R_2$ or $R_3$ include hydrogen, halo, nitro, carbamoyl, N-($C_{1-4}$alkyl)carbamoyl, NN-(di$C_{1-4}$alkyl)carbamoyl or $C_{1-4}$alkoxycarbonyl. Preferably hydrogen, halo, nitro, carbamoyl, N-ethylcarbamoyl, NN-dimethylcarbamoyl, N-methyl-N-ethylcarbamoyl, methoxycarbonyl or ethoxycarbonyl. More preferably hydrogen, halo or nitro. More preferably hydrogen, chloro or nitro. Most preferably either $R_1$ is halo, preferably chloro, $R_2$ is halo, preferably chloro and $R_3$ is hydrogen or $R_1$ is hydrogen, $R_2$ is nitro and $R_3$ is hydrogen.

Examples of suitable values for $R_4$ include indole, N-($C_{1-4}$alkyl) indole, $C_{5-7}$carbocyclic ring or aryl, either of which can be optionally substituted by halo, $C_{1-4}$alkyl, or $C_{1-4}$alkoxy. Preferably $R_4$ is indole, N-methylindole, cyclopentyl, cyclohexyl, phenyl or naphthyl, optionally substituted as defined above. More preferably $R_4$ is indole, N-methylindole, cyclohexyl, or phenyl, optionally substituted as defined above. More preferably $R_4$ is indole, N-methylindole, or phenyl, optionally substituted as defined above. More preferably $R_4$ is phenyl, optionally substituted as defined above. Most preferable $R_4$ is phenyl substituted with halo, preferably chloro.

Examples of suitable values for $R_5$ include hydrogen, $C_{1-4}$alkyl, $R_6CH_2$— or $R_6C(O)$—. Preferably $R_5$ is hydrogen, methyl, $R_6CH_2$— or $R_6C(O)$—. Most preferably $R_5$ is $R_6C(O)$—.

Examples of suitable values for $R_6$ include aryl, heteroaryl, heterocyclyl, amino-$C_{3-6}$alkyl, N-($C_{1-4}$alkyl) amino$C_{3-6}$alkyl, NN-(di$C_{1-4}$alkyl)amino$C_{3-6}$alkyl, or $R_7$. Preferably $R_6$ is aryl, heteroaryl, heterocyclyl, (NN-dimethyl)aminopropyl or $R_7$. More preferably $R_6$ is aryl, heteroaryl, heterocyclyl or $R_7$. More preferably $R_6$ is aryl and heteroaryl. Most preferably $R_6$ is aryl, preferably phenyl.

Examples of substituents on the aryl ring systems of $R_6$ include nitro, $C_{1-4}$alkyl, $C_{1-4}$alkoxy, halo, ($C_{1-4}$alkyl) sulfanyl. Preferably nitro, $C_{1-4}$alkyl, $C_{1-4}$alkoxy or methylsulfanyl. More preferably nitro or $C_{1-4}$alkoxy. Most preferably nitro or methoxy. More preferable substitution patterns on a phenyl group in $R_6$ are 2-nitro-4,5-dimethoxy, 2-methyl-3-nitro, 2-methoxy, 2,4-dimethyl, 4,5-dimethoxy-2-nitro or 2-methylsulfanyl. Most preferred is 2-nitro-4,5-dimethoxy.

Examples of suitable values for heteroaryl rings at $R_6$ include: furan, thiophene, pyrrole, pyrazole, isoxazole, thiazole, thiadiazole, pyridine, pyridazine, benzofuran, 4-oxo 4H-1-benzopyran. Heteroaryl ring systems with one or two heteroatoms are preferred. Heteroaryl ring systems with one heteroatom are most preferred.

Examples of suitable values for substituents on ring carbon atoms in heterocyclic rings of $R_6$ include, $C_{1-4}$alkyl, $C_{1-4}$alkoxy, halo, hydroxy, oxo or $C_{1-4}$alkylcarbonyl.

Examples of suitable values for $R_8$ include amino, guanadino and imidazolo, any of which can be mono or di-N-substituted with $C_{1-4}$alkyl. More preferably $R_8$ is guanadino or amino, substituted as defined above. Preferably $R_8$ is N-($C_{1-4}$alkyl)amino or amino. Most preferably $R_8$ is amino.

Examples of suitable values for $R_9$ include $C_{5-7}$alkyl, a $C_{5-10}$ membered carbocyclic ring and aryl, any of which can be optionally substituted with $C_{1-4}$alkyl. Preferably $R_9$ is 3-propylbutyl, 2,2 dimethylpropyl, a $C_{5-10}$ membered carbocyclic ring, or aryl. More preferably $R_9$ is cyclohexyl, cycloheptyl, adamantyl or aryl. Even more preferably $R_9$ is cyclohexyl or aryl. Yet more preferably $R_9$ is aryl. Most preferably $R_9$ is phenyl.

Examples of suitable values for $R_{10}$ include $C_{1-4}$alkyl or a $C_{3-7}$carbocyclic ring. More preferably $R_{10}$ is a $C_{3-7}$carbocyclic ring or a branched $C_{1-4}$alkyl chain. Even more preferably $R_{10}$ is a $C_{3-7}$carbocyclic ring. Most preferably $R_{10}$ is cyclohexyl.

Examples of suitable values for $R_{11}$ include hydrogen, halo, $C_{1-4}$alkyl, or $C_{1-4}$alkoxy. More preferably $R_{11}$ is hydrogen or $C_{1-4}$alkyl. Most preferably $R_{11}$ is hydrogen.

Examples of suitable values for $R_{12}$ are hydrogen or methyl or when $R_{12}$ is —$CH_2$—, $L_2$ is hydrogen and s is 1, $R_{12}$ together with $L_2$ forms a six membered nitrogen containing ring Preferably $R_{12}$ and $L_2$ are both hydrogen.

Examples of suitable values for $R_{13}$ are hydrogen or methyl or when $R_{13}$ is —$CH_2$—, $L_4$ is hydrogen and s is 1, $R_{13}$ together with $L_4$ forms a six membered nitrogen containing ring Preferably $R_{13}$ and $L_4$ are both hydrogen.

Preferably n is 1
Preferably p is 1
Preferably q is 2–4. Most preferable q is 4.
Preferably r is 1.
Preferably s is 1.

It is to be understood that, insofar as certain of the compounds of Formula (1) defined above may exist in optically active or racemic forms by virtue of one or more asymmetric carbon atoms, the invention includes in its definition any such optically active or racemic form which possesses the property of inhibiting MDM2 interactions. The synthesis of optically active forms may be carried out by standard techniques of organic chemistry well known in the art, for example by synthesis from optically active starting materials or by resolution of a racemic form. Similarly, inhibitory properties against MDM2 interactions may be evaluated using the standard laboratory techniques referred to hereinafter.

When $R_6$ is other than $R_7$ then the following stereochemistry is preferred, in the group —$N(L_1)CH((CH_2)_nR_4)$CO—, in formula (1):

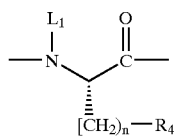

Formula (X)

A particular group of compounds of the invention include for example, a compound of formula (1) wherein $R_5$ is hydrogen or $C_{1-4}$ alkyl, or a pharmaceutically acceptable salt, prodrug or solvate thereof, wherein either:

(a) $R_1$ is hydrogen; $R_2$ is nitro; $R_3$ is hydrogen; $R_4$ is indole, N-($C_{1-4}$alkyl)indole or cyclohexyl; $R_5$ is hydrogen or methyl; $L_1$ is hydrogen and n is 1 or 2; and where the optical centre represented in the Formula (X) is in the S configuration; or (b) $R_1$ is halo; $R_2$ is halo; $R_3$ is hydrogen; $R_4$ is indole, N-($C_{1-4}$alkyl)indole or cyclohexyl; $R_5$ is hydrogen or methyl; $L_1$ is hydrogen and n is 1 or 2; and where the optical centre represented in the Formula (X) is in the S configuration.

A further preferred group of compounds of the invention include, for example a compound of formula (1) wherein $R_5$ is $R_6C(O)$— or $R_6CH_2$—, or a pharmaceutically acceptable salt, prodrug or solvate thereof, wherein either:

(a) $R_1$ is hydrogen; $R_2$ is nitro; $R_3$ is hydrogen; $R_4$ is indole; N-($C_{1-4}$alkyl)indole, halo-phenyl or cyclohexyl; $R_5$ is $R_6C(O)$— or $R_6CH_2$—; $R_6$ is substituted phenyl; $L_1$ is hydrogen or methyl and n is 1 or 2; and where the optical centre represented in the Formula (X) is in the S configuration; or (b) $R_1$ is hydrogen; $R_2$ is nitro; $R_3$ is hydrogen; $R_4$ is indole; N-($C_{1-4}$alkyl)indole; halo-phenyl or cyclohexyl, $R_5$ is $R_6C(O)$— or $R_6CH_2$—, $R_6$ is a substituted heterocycle; $L_1$ is hydrogen or methyl and n is 1 or 2; and wherein the optical centre represented in the Formula (X) is in the S configuration.

A further preferred group of compounds of the invention include, for example a compound of formula (1) wherein $R_5$ is $R_6C(O)$— and $R_6$ is $R_7$, or a pharmaceutically acceptable salt, prodrug or solvate thereof, wherein either:

(a) $R_1$ is hydrogen; $R_2$ is nitro; $R_3$ is hydrogen; $R_4$ is indole; N-($C_{1-4}$alkyl)indole; cyclohexyl or halo-phenyl; $R_5$ is $R_6C(O)$—; $R_6$ is $R_7$; $R_7$ is of formula (2); $R_8$ is amino; $R_9$ is an optionally substituted aryl group; $R_{11}$ is hydrogen; $A_1$ is oxygen or a bond; n is 1 or 2; p is 1; q is 2–4 and $L_1$ and $L_2$ and $L_3$ are independently hydrogen or methyl; or (b) $R_1$ is hydrogen; $R_2$ is nitro; $R_3$ is hydrogen; $R_4$ is indole; N-($C_{1-4}$alkyl)indole; cyclohexyl or halo-phenyl; $R_5$ is $R_6C(O)$—; $R_6$ is $R_7$; $R_7$ is of formula (2); $R_8$ is amino; $R_9$ is an optionally substituted heterocyclic group; $R_{11}$ is hydrogen; $A_1$ is oxygen or a bond; n is 1 or 2; p is 1; q is 2–4 and $L_1$ and $L_2$ and $L_3$ are independently hydrogen or methyl.

A further preferred group of compounds of the invention include, for example a compound of formula (1) wherein $R_5$ is $R_6CH_2$— and $R_6$ is $R_7$, or a pharmaceutically acceptable salt, prodrug or solvate thereof, wherein:

(a) $R_1$ is hydrogen; $R_2$ is nitro; $R_3$ is hydrogen; $R_4$ is indole; N-($C_{1-4}$alkyl)indole; cyclohexyl or halo-phenyl; $R_5$ is $R_6CH_2$—; $R_6$ is $R_7$; $R_7$ is of formula (3); $R_{10}$ is either a $C_{3-7}$ carbocyclic ring or a $C_{1-4}$alkyl chain; $R_{11}$ is hydrogen; $L_4$ is hydrogen or methyl and r is 1.

A more preferred compound of the invention is a compound of formula (1) wherein $R_5$ is $R_6C(O)$— and $R_6$ is a substituted phenyl group, or a pharmaceutically acceptable salt, prodrug or solvate thereof, wherein;

$R_1$ is hydrogen; $R_2$ is nitro; $R_3$ is hydrogen; $R_4$ is indole; N-($C_{1-4}$alkyl)indole; or 4-chloro-phenyl; $R_5$ is $R_6C(O)$—; $R_6$ is 4,5-dimethoxy-2-nitrophenyl; $L_1$ is hydrogen or methyl; n is 1 and where the optical centre represented in the Formula (X) is in the S configuration.

A further more preferred compound of the invention is a compound of formula (1) wherein $R_5$ is $R_6C(O)$— and $R_6$ is $R_7$ and $R_7$ is of formula (2), or a pharmaceutically acceptable salts, prodrugs or solvates thereof, wherein:

$R_1$ is hydrogen; $R_2$ is nitro; $R_3$ is hydrogen; $R_4$ is indole; N-($C_{1-4}$alkyl)indole; phenyl; 4-chloro-phenyl or cyclohexyl; $R_5$ is $R_6C(O)$—; $R_6$ is $R_7$; $R_7$ is of formula (2); $R_8$ is amino; $A_1$ is oxygen or a bond, $R_9$ is phenyl or cyclohexyl; $R_{11}$ is hydrogen; $L_1$, $L_2$ and $L_3$ are independently hydrogen or methyl; n is 1; q is 2–4 and p is 0–1.

Particular compounds of the invention are;
2-methyl-3-nitrobenzoyl-Trp-piperazine-4-nitrophenyl;
2,4-dimethyl-benzoyl-Trp-piperazine-4-nitrophenyl;
5-bromo-2-furoyl-Trp-piperazine-4-nitrophenyl;

2-methoxybenzoyl-Trp-piperazine-4-nitrophenyl;
dimethoxynitrobenzoyl-Trp-piperazine-4-nitrophenyl;
2-methyl-3-furoyl-Trp-piperazine-4-nitrophenyl;
tiophene-3-carboxyl-Trp-piperazine-4-nitrophenyl;
2-(methylthio)-nicotinoyl-Trp-piperazine-4-nitrophenyl;
3-chlorothiphene-2-carboxyl-Trp-piperazine-4-nitrophenyl;
2,5-dimethoxybenzoyl-Trp-piperazine-4-nitrophenyl;
2-benzofuroyl-Trp-piperazine-4-nitrophenyl;
N-methylpyrrole-2-carboxyl-Trp-piperazine-4-nitrophenyl;
2-bromo-5-methoxybenzoyl-Trp-piperazine-4-nitrophenyl;
thiophene-2-carboxyl-Trp-piperazine-4-nitrophenyl;
5-chlorothiophene-2-carboxyl-Trp-piperazine-4-nitrophenyl;
2-methoxy-4-nitrobenzoyl-Trp-piperazine-4-nitrophenyl;
2-furylcarbonyl-Trp-piperazine-4-nitrophenyl;
6-methylpicoliny-Trp-piperazine-4-nitrophenyl;
3-methoxy-2-nitrobenzoyl-Trp-piperazine-4-nitrophenyl;
Dimethoxynitrobenzoyl-(D)Trp-piperazine-4-nitrophenyl;
4-oxo-4H-1-benzopyran-2-caboxyl-Trp-piperazine-4-nitrophenyl;
5-nitro-2-furoyl-Trp-piperazine-4-nitrophenyl;
1,2,3-thiadiazole-4-carboxyl-Trp-piperazine-4-nitrophenyl;
Z-Lys-(NMe)Phe-Trp-piperazine-4-nitrophenyl;
cyclohexylacetyl-(D)Lys-(D)NMe-Phe-(D)Trp-piperazine-4-nitrophenyl;
adamantaneacetyl-(D)Lys-(D)NMe-Phe-(D)Trp-piperazine-4-nitrophenyl;
cycloheptanoyl-(D)Lys-(D)NMe-Phe-(D)Trp-piperazine-4-nitrophenyl;
2-propylpentanoyl-(D)Lys-(D)NMe-Phe(D)Trp-piperazine-4-nitrophenyl;
Z-(D)NMe-Lys-(D)NMe-Phe-(D)Trp-piperazine-4-nitrophenyl;
Me$_2$CHCH$_2$(D,L)NME-Phe{CH$_2$NH}(D)Trp-piperazine-4-nitrophenyl;
Z-LYS-(NMe)Phe-(D)Trp-piperazine-4-nitrophenyl;
cyclohexyl-(D)Lys-(D)(NMe)Phe-(D)Trp-piperazine-4-nitrophenyl;
T-butylacetyl-(D)Lys-(D)NMePhe-(D)Trp-piperazine-4-nitrophenyl;
cyclohexyl-(D)Lys-(D)NMe-Phe-(D)Phe(4-Cl)-piperazine-dichlorophenyl;and
cyclohexyl-(D)Lys-(D)NMePhe-(D)Tyr(Et)-piperazine-4-nitrophenyl;
or a pharmaceutically acceptable salt, prodrug or solvate thereof.

Further particular compounds of the invention are:
4,5-dimethoxy-2-nitrobenzoyl-Phe(4-Cl)-piperazine-4-nitrophenyl;
4,5-dimethoxy-2-nitrobenzoyl-NMe-Trp-piperazine-4-nitrophenyl;
4,5-dimethoxy-2-nitrobenzoyl-(D)(N$^{in}$-Me)Trp-piperazine-4-nitrophenyl;
Z-(D)(NMe)Dab-(NMe)(D)Phe-(D)Trp-piperazine-4-nitrophenyl;
Z-NMe(D)Lys-NMe(D)Phe-(D)Phe(4-Cl)-piperazine-4-nitrophenyl;
cyclohexyl-CO-(D)Lys-(D)NMe-Phe-Cha-piperazine-4-nitrophenyl;
cyclohexyl-(D)Lys-(D)(NMe)Phe-(D)Phe(4-Cl)-piperazine-4-nitrophenyl;
cyclohexyl-CH$_2$-(D,L)NMe-Phe{CH$_2$NH}(D)Trp-piperazine-4-nitrophenyl; and
cyclohexyl-(D)Lys-(D)(NMe)Phe-(D)hPhe-piperazine-4-nitrophenyl;
or a pharmaceutically acceptable salt, prodrug or solvate thereof.

A suitable pharmaceutically-acceptable salt of a compound of the formula (1) is, for example, an acid-addition salt of a compound of the Formula (1) which is sufficiently basic, for example an acid-addition salt with an inorganic or organic acid such as hydrochloric, hydrobromic, sulphuric, trifluoroacetic, citric or maleic acid; or, for example a salt of a compound of the Formula (1) which is sufficiently acidic, for example an alkali or alkaline earth metal salt such as a calcium or magnesium salt, or an ammonium salt, or a salt with an organic base such as methylamine, dimethylamine, trimethylamine, piperidine, morpholine or tris-(2-hydroxyethyl)amine.

Various forms of prodrugs are known in the art, for example in-vivo hydrolysable esters.

In vivo hydrolysable derivatives include, in particular, pharmaceutically acceptable derivatives that may be oxidised or reduced in the human body to produce the parent compound or esters that hydrolyse in the human body to produce the parent compound. Such esters can be identified by administering for example, intravenously to the test animal, the compound under test and subsequently examining the test animal's body fluids. Suitable in vivo hydrolysable esters for hydroxy include acetyl and for carboxyl include, for example, alkyl esters, dialkylaminoalkoxy esters, esters of formula —C(O)—O—CH2C(O)NRa"Rb" where Ra" and Rb" are, for example, selected from hydrogen and C1–4 alkyl, and C1–6alkoxy methyl esters for example methoxymethyl, C1–6alkanoyloxymethyl esters for example pivaloyloxymethyl, phthalidyl esters, C3–8 cycloalkoxycarbonyloxyC1–6alkyl esters for example 1-cylohexylcarbonyloxyethyl; 1,3-dioxolan-2-ylmethyl esters for example 5-methyl-1,3-dioxolan-2-ylmethyl; and C1–6-alkoxycarbonyloxyethyl esters for example 1-methoxycarbonyloxyethyl.

For examples of prodrug derivatives see:

a) Design of Prodrugs, edited by H. Bundgaard, (Elsevier, 1985) and Methods in Enzymology, Vol. 42, p. 309–396, edited by K. Widder, et al. (Academic Press, 1985);

b) A Textbook of Drug Design and Development, edited by Krogsgaard-Larsen and H. Bundgaard, Chapter 5 "Design and Application of Prodrugs", by H. Bundgaard p. 113–191 (1991);

c) H. Bundgaard, Advanced Drug Delivery Reviews, 8, 1–38 (1992);

d) H. Bundgaard, et al., Journal of Pharmaceutical Sciences, 77, 285 (1988); and e) N. Kakeya, et al., Chem Pharm Bull, 32, 692 (1984).

It will also be understood that certain compounds of the present invention may exist in solvated, for example hydrated, as well as unsolvated forms. It is to be understood that the present invention encompasses all such solvated forms which possess the property of inhibiting MDM2 interactions.

In another aspect the present invention provides a process for preparing a compound of the Formula (1) or a pharmaceutically acceptable salt, prodrug or ester thereof which process comprises deprotecting a compound of the Formula (7):

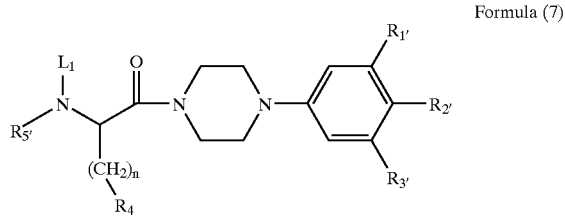

Formula (7)

wherein n, $L_1$ and $R_4$ are as hereinabove defined and $R_{1'}$ is $R_1$ or protected $R_1$, $R_{2'}$ is $R_2$ or protected $R_2$, $R_{3'}$ is $R_3$ or protected $R_3$ and $R_{5'}$ is $R_5$ or protected $R_5$; wherein at least one protecting group is present; and thereafter if necessary:

i) forming a pharmaceutically-acceptable salt,
ii) forming a prodrug, and/or
iii) forming a solvate.

Protecting groups may in general be chosen from any of the groups described in the literature or known to the skilled chemist as appropriate for the protection of the group in question, and may be introduced by conventional methods.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience in which "lower" signifies that the group to which it is applied preferably has 1–4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxy protecting group may be the residue of an ester-forming aliphatic or araliphatic alcohol or of an ester-forming silanol (the said alcohol or silanol preferably containing 1–20 carbon atoms).

Examples of carboxy protecting groups include straight or branched chain $C_{1-12}$alkyl groups (for example isopropyl, t-butyl); lower alkoxy lower alkyl groups (for example methoxymethyl, ethoxymethyl, isobutoxymethyl); lower aliphatic acyloxy alkyl groups, (for example acetoxymethyl, propionyloxymethyl, butyryloxymethyl, pivaloyloxymethyl); lower alkoxycarbonyloxy lower alkyl group (for example 1-methoxycarbonylethyl, 1-ethoxycarbonylethyl); phenyl lower alkyl groups (for example benzyl, p-methoxybenzyl, o-nitrobenzyl, p-nitrobenzyl, benzhydryl and phthalidyl); tri(lower alkyl) silyl groups (for example trimethylsilyl and t-butyldimethylsilyl); tri(lower alkyl)silyl lower alkyl groups (for example trimethylsilylethyl); and $C_{2-6}$alkenyl groups (for example allyl and vinylethyl).

Methods particularly appropriate for the removal of carboxy protecting groups include for example acid-, base-, metal- or enzymically-catalysed hydrolysis.

Example of hydroxy protecting groups include lower groups (for example t-butyl), lower alkenyl groups (for example allyl); lower alkanoyl groups (for example acetyl); lower alkoxycarbonyl groups (for example t-butoxycarbonyl); lower alkenyloxycarbonyl groups (for example allyloxycarbonyl); phenyl lower alkoxycarbonyl group (for example benzoyloxycarbonyl, p-methoxybenzyloxycarbonyl, o-nitrobenzyloxycarbonyl, p-nitrobenzyloxycarbonyl); tri lower alkylsilyl (for example trimethylsilyl, t-butyldimethylsilyl) and phenyl lower alkyl (for example benzyl) groups.

Examples of amino protecting groups include formyl, aralkyl groups (for example benzyl and substituted benzyl, p-methoxybenzyl, nitrobenzyl and 2,4-dimethoxybenzyl, and triphenylmethyl); di-p-anisylmethyl and furylmethyl groups; lower alkoxycarbonyl (for example t-butoxycarbonyl); lower alkenyloxycarbonyl (for example allyloxycarbonyl); phenyl lower alkoxycarbonyl groups (for example benzyloxycarbonyl, p-methoxybenzyloxycarbonyl, o-nitrobenzyloxycarbonyl, p-nitrobenzyloxycarbonyl; trialkylsilyl (for example trimethyisilyl and t-butyldimethylsilyl); alkylidene (for example methylidene); benzylidene and substituted benzylidene groups.

Methods appropriate for removal of hydroxy and amino protecting groups include, for example, acid-, base-, metal- or enzymically-catalysed hydrolysis, for groups such as p-nitrobenzyloxycarbonyl, hydrogenation and for groups such as o-nitrobenzyloxycarbonyl, photolytically.

The reader is referred to Advanced Organic Chemistry, $4^{th}$ Edition, by Jerry March, published by John Wiley & Sons 1992, for general guidance on reaction conditions and reagents. The reader is referred to Protective Groups in Organic Synthesis $2^{nd}$ Edition, by Green et al, published by John Wiley & Sons for general guidance on protecting groups.

Compounds of the formula (1) and (7) can be formed by:
i) reacting a carboxylic acid of formula (8) or a reactive derivative thereof with a piperazine of formula (9)

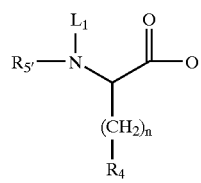

Formula (8)

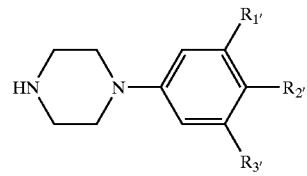

Formula (9)

wherein $L_1$, n, $R_4$, $R_{1'}$–$R_{3'}$ and $R_{5'}$ are as hereinabove defined.

A suitable reactive derivative of an acid of the Formula III is, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an active ester, for example an ester formed by the reaction of the acid with a phenol such as pentafluorophenol, with an ester such as pentafluorophenyl trifluoroacetate or with an alcohol such as N-hydroxybenzotriazole; an acyl azide, for example an azide formed by the reaction of the acid and an azide such as diphenylphosphoryl azide; an acyl cyanide, for example a cyanide formed by the reaction of an acid and a cyanide such as diethylphosphoryl cyanide; or the product of the reaction of the acid and a carbodiimide such as dicyclohexylcarbodiimide.

The reaction between compounds of the formulae (8) and (9) is carried out under conditions known for peptide bond formation. Typically the reaction is carried out in an organic solvent such as DMF or DMA. A small amount of THF and DMSO may be added as well. The reaction is usually carried out in the presence of an activating agent such as O-(7-azabenzotriazol-1-yl)-1,1,3,3-tetramethyluronium hexafluorophosphate (HATU) and a base, particularly an amine base, for example diisopropylethylamine. In addition 1-hydroxy-7-azabenzotriazole (HOAT) may be added as catalyst. The reaction is normally carried out in a temperature range of 0 to 80° C., preferably at around ambient temperature. 2-(1H-Benzotriazol-1yl)-1,1,3,3-tetramethyluroniunhexafluorophosphate (HBTU), may be used instead of HATU in which case 1-hydroxybenzotriazole (HOBt) is generally used as catalyst.

The compound of the formula (8) is conveniently prepared by solid phase organic synthesis on a polymer resin. The resin is preferably one that can be removed with mild acid such as chlorotritylchloride resin. For example of other suitable polystyrene resins see the Nova Biochem Combinatorial Chemistry Catalogue February 1997.

The synthesis of a compound of the formula (8) is normally started with an amino acid which has a —$(CH_2)_n$ $R_4$ side chain. The amino acid functional groups not taking part in the reaction are protected by various functional groups. For example, the N-terminal and side chain amino groups may be protected by using 9-fluoroenylmethoxycarbonyl (Fmoc), t-butoxycarbonyl (Boc), biphenylisopropoxycarbonyl (Bpoc), 2-[3,5-dimethoxyphenyl]propyl-2-oxycarbonyl (Ddz), adamantyloxycarbonyl (Adoc), allyloxycarbonyl (Aloc), 2,2,2-trichloroethoxycarbonyl (Troc), benzyloxycarbonyl and various substituted benzyloxycarbonyl groups. These protected groups can be cleaved when required by the standard techniques (e.g. acid or base treatment, catalytic hydrogenolysis and Pd(0) treatment or zinc/acetic acid treatment). The choice of protecting group depends to a large extent on the type of resin used. When the resin is chlorotrityichoride the preferred amino protecting group is Fmoc.

The protected amino acid is then mixed with the resin so that its reacts with the resin through its carboxy group. When the resin is chlorotrityl resin, the reaction between amino acid and resin is conventionally carried out in an organic solvent such as DMF in the presence of a base such as DIPEA. The amino-protecting group is then removed so that the $R^{5'}$ can be introduced if it is other than hydrogen. The protecting group cleavage reactions can be performed at temperatures in the range of 4° C. to 40° C. (preferably at or about ambient temperature) and over a period of time in the range of 10 minutes to 24 hours.

The introduction of the $R_{5'}$ group when $R_{5'}$ is of the formula $R_6C(O)$— is carried out using standard methods know for the formation of an amide bond, as shown for example in the presence of HBTU as described above.

When $R_6$ is of the formula $R_7$ the group $R_6CO$— can gradually be built up with subsequent amide bond forming reactions. For example the group $NH(L_2)$—$CH(CH_2Ph)$—$CO$— may be introduced onto the amino acid attached to the resin by reacting a compound of the formula $PN(L_2)$—$CH(CH_2Ph)COOH$ (wherein P is an amino-protecting group), with the latter compound under amide bond-forming conditions. The amino-protecting group can then be removed and the resulting compound reacted with a compound of the formula $PN(L_3)CH((CH_2)_nR_8)COOH$ under similar conditions. Again the amino-protecting group can be removed and the resulting compound reacted with a compound of the formula $R_9(CH_2)_pA_1$—$COOH$. Alternatively the group $R_7COOH$ could be formed itself through subsequent amide-bond forming reactions and then introduced in one step onto the amino acid that is attached to the resin.

The resin is then removed, which in the case of chlorotrityl resin involves treating it with acetic acid and trifluoroethanol, to give a compound of the formula (8).

For further information on the formation of amide bonds see the procedures disclosed in "Solid Phase Peptide Synthesis: A practical approach" by Atherton and Sheppard (published by IRL press at Oxford University Press, 1989). "Solid Phase Peptide Synthesis" by Stewart and Young (published by the Pierce Chemical Company, Illinois, 1984), "Principles of Peptide Synthesis" (published by Springer-Verlag, Berlin, 1984), and a series of books "Amino Acids, Peptides and Proteins" (volumes 1–25; volume 25 published in 1994) (published by the Royal Society of Chemistry, Cambridge, UK).

Similar reaction conditions can be used to synthesise a compound of the (8) without using a resin support.

When $R_{5'}$ is of the formula $R_6CH_2$—, a compound of the formula (8) may be prepared by reacting together a compound of the formula $R_6C(O)H$ and the appropriate amine under conditions known for the formation of a Schiff's base, followed by reduction of the Schiff's base to the methylamino group. The reaction is typically carried out in an organic solvent such as DMF or an alcohol such as methanol or ethanol. Suitable reducing agents include sodium trisacetoxyborohydride, sodium cyanoborohydride and sodium borohydride.

A compound of the formula (9) is conveniently prepared by reacting piperazine, in which one nitrogen is protected, with a group of the formula:

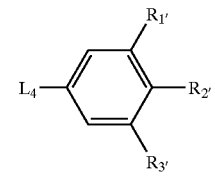

wherein $L_4$ is a leaving group and $R_{1'}$–$R_{3'}$ are as hereinabove defined. Preferably the leaving group is chloro. The reaction is generally carried out in an inert organic solvent such as toluene or methylformamide, in the presence of an organic base such as triethylamine or DBU, in a temperature range of 80–200° C., preferably at reflux.

Optional substituents in a compound of the formula (1) or (7) or intermediates in their preparation may be converted into other optional substituents. For example an hydroxy group could be alkylated to a methoxy group.

Various substituents may be introduced into compounds of the formulae (1) or (7) and intermediates in this preparation, when appropriate, using standard methods known in the art. For example, an acyl group or alkyl group may be introduced into an activated benzene ring using Friedel-Crafts reactions, a nitro group by nitration with concentrated nitric acid and concentrated sulphuric acid and bromination with bromine or tetra(n-butyl)ammonium tribromide.

It will be appreciated that, in certain steps in the reaction sequence to compounds of the formula (1), it will be necessary to protect certain functional groups in intermediates in order to prevent side reactions. Deprotection may be carried out at a convenient stage in the reaction sequence once protection is no longer required., In order to use a compound of the Formula (1), or a pharmaceutically-acceptable salt or in vivo cleavable ester thereof, for the therapeutic treatment (including prophylactic treatment) of mammals including humans, it is normally formulated in accordance with standard pharmaceutical practice as a pharmaceutical composition.

According to this aspect of the invention there is provided a pharmaceutical composition which comprises an amide derivative of the Formula (1), or a pharmaceutically-acceptable or in vivo cleavable ester thereof, as defined herein before in association with a pharmaceutically-acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically-acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gun tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipients which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedures well known in the art.

Compositions for administration by insufflation may be in the form of a finely divided powder containing particles of average diameter of, for example, 30 $\mu$m or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on Formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound of the Formula (1) will naturally vary according to the nature and severity of the conditions, the age and sex of the animal or patient and the route of administration, according to well known principles of medicine.

In using a compound of the Formula (1) for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred, particularly in tablet form. Typically, unit dosage forms will contain about 1 mg to 500 mg of a compound of this invention.

The compounds of this invention may be used in combination with other drugs and therapies used in the treatment of disease states which would benefit from the inhibition of the interaction of p53 and MDM2. For example, the compounds of the Formula (1) could be used in combination with drugs and therapies used in the treatment of cancers, including, but not limited to, breast cancer, sarcomas, osteosarcoma, testicular cancer or oesophageal cancer.

If formulated as a fixed dose such combination products employ the compounds of this invention within the dosage range described herein and the other pharmaceutically-active agent within its approved dosage range. Sequential use is contemplated when a combination formulation is inappropriate.

Although the compounds of the Formula (1) are primarily of value as therapeutic agents for use in warm-blooded animals (including man), they are also useful whenever it is required to inhibit the interaction of p53 and MDM2. Thus, they are useful as pharmacological standards for use in the development of new biological tests and in the search for new pharmacological agents.

In a further aspect of the invention there is provided a method of probing the biochemistry of MDM2 interactions using a compound of formula (1).

In a further aspect of the invention there is provided for use in the treatment of a warm-blooded animal, by therapy, a compound of formula (1), or a pharmaceutically acceptable salt, prodrug or solvate thereof as herein defined.

In a further aspect of the invention there is provided a method of treating cancers which comprises administering to a warm-blooded animal an effective amount of a compound of formula (4), formula (4)

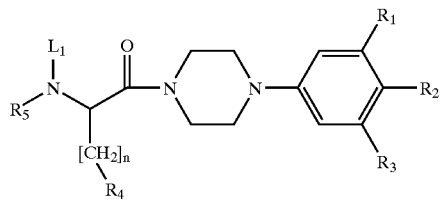

wherein:
$L_1$ is hydrogen or methyl;
$R_1$ and $R_2$ and $R_3$ are each independently hydrogen, halo, nitro, cyano, carbamoyl, N-($C_{1-4}$alkyl)carbamoyl, NN-(di$C_{1-4}$alkyl)carbamoyl or $C_{1-4}$alkoxycarbonyl;
$R_4$ is indole, N-($C_{1-4}$ alkyl) indole, $C_{5-7}$carbocyclic ring or aryl, any of which can be optionally substituted on ring carbon atoms with up to three substituents each independently selected from halo, $C_{1-4}$alkyl, or $C_{1-4}$alkoxy;
$R_5$ is hydrogen, $C_{1-4}$alkyl, $R_6CH_2$— or $R_6C(O)$—;
$R_6$ is aryl, heteroaryl, heterocyclyl, amino$C_{3-6}$alkyl, N-($C_{1-4}$alkyl)amino$C_{3-6}$alkyl, NN-(di$C_{1-4}$alkyl)amino$C_{1-4}$alkyl, or $R_7$; wherein the aryl, heteroaryl or heterocyclyl rings may be optionally substituted with up to three substituents independently selected from nitro, $C_{1-4}$alkyl, $C_{1-4}$alkoxy, halo, ($C_{1-4}$alkyl)sulfanyl, $C_{1-4}$alkoxycarbonyl, N-($C_{1-4}$alkyl)carbamoyl, NN-(di$C_{1-4}$alkyl)carbamoyl, N-($C_{1-4}$alkyl)amino or NN-(di$C_{1-4}$alkyl)amino;
wherein $R_7$ is either a group of formula (5) of formula (6):

Formula (5)

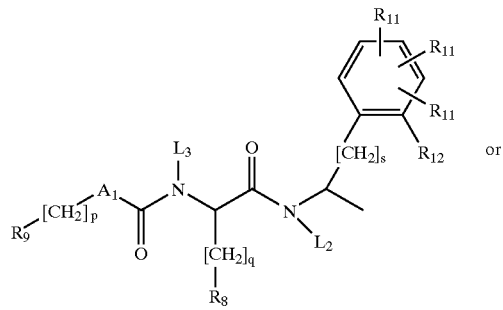

or

Formula (6)

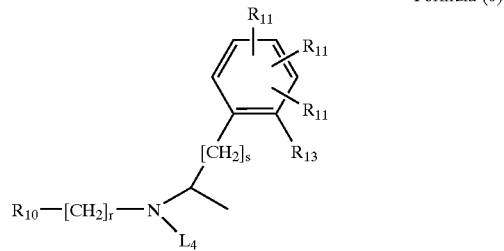

wherein:

$L_2$, $L_3$ and $L_4$ are each independently hydrogen or methyl;

$R_8$ is amino, guanadino, imidazolo, any of which can be mono or di-N-substituted with $C_{1-4}$alkyl;

$A_1$ is oxygen or a direct bond;

$R_9$ is a $C_{5-8}$ membered mono-carbocyclic ring, a $C_{6-10}$ membered bi-carbocyclic ring, $C_{8-12}$ membered tri-carbocyclic ring, $C_{5-7}$alkyl or aryl, any of which can be optionally mono, bi or tri substituted by $C_{1-4}$ alkyl;

$R_{10}$ is $C_{1-6}$alkyl or a $C_{3-8}$mono-carbocyclic ring;

$R_{11}$ is hydrogen, halo, $C_{1-4}$alkyl, or $C_{1-4}$alkoxy;

$R_{12}$ is hydrogen or methyl or ethyl or $R_{12}$ together with $L_2$ forms a $C_{5-7}$ nitrogen-containing heterocyclic ring;

$R_{13}$ is hydrogen or methyl ethyl or $R_{13}$ together with $L_4$ forms a $C_{5-7}$ nitrogen-containing heterocyclic ring;

n is 0, 1 or 2;

p is 0, 1 or 2;

q is an integer from 1 to 6 r is 0, 1 or 2;

s is 0, 1 or 2;

provided that when $R_6$ is aryl, heteroaryl, heterocyclyl, amino$C_{3-6}$alkyl, N-($C_{1-4}$alkyl)amino$C_{3-6}$alkyl or NN-(di$C_{1-4}$alkyl)amino$C_{3-6}$alkyl then $R_5$ is other than $R_6CH_2$—; or a pharmaceutically acceptable salt, prodrug or solvate thereof.

In a further aspect of the invention there is provided a method of treating cancers, mediated by wild type or altered MDM2, which comprises administering to a warm-blooded animal an effective amount of a compound of formula (4), or a pharmaceutically acceptable salt, prodrug or solvate thereof as herein defined.

In a further aspect of the invention there is provided the use of a compound of formula (4) or a pharmaceutically acceptable salt, prodrug or solvate thereof as herein defined, in the manufacture of a medicament for use in the treatment of cancer.

In a further aspect of the invention there is provided the use of a compound of formula (4) or a pharmaceutically acceptable salt, prodrug or solvate thereof as herein defined, in the manufacture of a medicament for use in the treatment of cancer, mediated by wild type or altered MDM2.

In a further aspect of the invention there is provided the use of a compound of formula (4) or a pharmaceutically acceptable salt, prodrug or solvate thereof as herein defined in the manufacture of a medicament for the treatment of cancer in a warm-blooded animal.

In a further aspect of the invention there is provided the use of a compound of formula (4) or a pharmaceutically acceptable salt, prodrug or solvate thereof as herein defined in the manufacture of a medicament for the treatment of cancers, mediated by wild-type or altered MDM2, in a warm-blooded animal.

In a further aspect of the invention there is provided a pharmaceutical composition comprising a compound of formula (4), or a pharmaceutically acceptable salt, prodrug or solvate thereof as herein defined, in admixture with a pharmaceutically-acceptable diluent or carrier for the treatment of cancer in a warm-blooded animal.

In a further aspect of the invention there is provided a pharmaceutical composition comprising a compound of formula (4), or a pharmaceutically acceptable salt, prodrug or solvate thereof, in admixture with a pharmaceutically-acceptable diluent or carrier for the treatment of cancer, mediated by wild-type or altered MDM2, in a warm-blooded animal.

The following biological assay provides a method of measuring the inhibition of the interaction of p53 with MDM2.

Biological Assays

Measurement of the Inhibition of p53/MDM2 Interaction

The inhibition of the p53/MDM2 interaction by compounds was measured using a modified ELISA assay using a histidine tagged MDM2 [MDM2 (1–118) 6 his], a p53 GST fusion protein (GST-p53) and a nickel chelate-alkaline phosphatase (NTA-AP).

The human MDM2 N-terminal fragment encompassing amino acids 1–118 and immediately followed by a C-terminal 6-histidine tag sequence and then a stop codon was generated by PCR from a human placental cDNA library. The PCR product was initially cloned into pCR2.1 vector (Invitrogen) following the manufacturer's protocol. DNA sequencing confirmed a MDM fragment sequence identical to that of published MDM2 (EMBL accession no. Z12020). The MDM2-6His fragment was then subcloned into pTB375 *E. coli* expression vector to produce the expression vector pTB375-MDM2-6His (1–118) clone no. 11. The pTB375 vector is a modified T7 (Studier) Expression vector. Expression grows were performed in *E. coli* strain BL21/DE3 (obtained from Novagen Inc.) and expression of the recombinant protein was induced by addition of IPTG (isopropyl-β-D-1-thiogalactopyranoside). MDM2 (1–118) 6 his was purified from *E. coli* lysates using Ni-NTA beads (Qiagen).

The background vector for generation of pTB375 was pZEN0042 (pICI0042), described fully in UK patent application GB 2253852. Briefly, pZEN0042 contains the tetA/tetR inducible tetracycline resistance sequence from plasmid RP4 and the cer stability sequence from plasmid pKS492 in a pAT153 derived background. pTB375 was generated by the addition of an expression cassette consisting of the T7 gene 10 promoter, multiple cloning site and T7 gene 10 termination sequence. In addition, a terminator sequence designed to reduce transcriptional readthrough from the background vector was included upstream of the expression cassette.

A DNA fragment encoding aa1–50 of p53 followed by a stop codon was generated by PCR using vector pHp53B (ATCC clone no. 57255) as template. The PCR product was initially cloned into pCR2.1 vector (Invitrogen) following the manufacturer's protocol. DNA sequencing confirmed a p53 sequence identical to that of published p53 (EMBL accession no. X04269).

The p53 fragment was then subcloned into pGEX-4T1 *E coli* expression vector (Pharmacia) to produce the expression vector pGEX-4T1-p53(1–50) clone no. 7. The sequence of the expression vector at the junction of the GST and p53 sequences was as follows:

GST seq . . . CTG GTT CCG CGT GGA TCC ATG . . . (SEQ ID NO: 1)

(ATG is aa1 of p53, GGA TCC is the conserved BamHI cloning site)

Expression grows were performed in *E. coli* strain DH5alpha and expression of the recombinant protein was induced by addition of IPTG. GST-p53(1–50) was purified using glutathione-sepharose beads (Pharmacia). The procedures used for expressing the GST fusion protein are therefore analogous procedures to those disclosed by J. Han et al., Journal of Biological Chemistry, 1996, 271, 2886–2891.

In the assay the following solutions were used:

Stock GST-p53 (6.1 mg/ml/~200 uM) diluted 2706 fold using $H_2O$;

Stock MDM2-6His (1.1 mg/ml, ~70 uM) diluted 933 fold using $H_2O$;

Stock NTA-AP was made by reconstituting lyophilised Ni-NTA-AP (Qiagen 34510-200 μg) in 500 ul distilled water and stored as frozen aliquots. It was frehly diluted 1:1000 using phosphate buffered saline (PBS) for use in the assay;

PNPP buffer—100 mM Tris HCl, pH 9.5, 100 mM NaCl, 5 mM $MgCl_2$;

2.5 mM Phosphatase substrate (Sigma 104 phosphatase substrate) was dissolved in PNPP buffer approximately 20 minutes prior to use; it was kept in the dark;

Double distilled water was used throughout the assay.

100 μl of 75 nM GST-p53 was added per well to a 96 well plate (Nunc Maxisorp) and the plate left at 4° C. overnight. Next day the fluid in the wells was removed and discarded and 100 μl 0.2% bovine serum albumin (BSA) in PBS was added to each well and left at room temperature for 1 hour. The fluid was then removed and discarded and each well was washed twice with 0.1% Tween in PBS. After removing and discarding the second tween/PBS wash, 10 μl of compound was added to each well, followed by 90 μl 75 nM MDM2-6His. The plate was then incubated at room temperature for 1.5 hours. After this time the fluid from each well was removed and discarded and each well was washed three times with 280 μl Tween/PBS. After removing and discarding the final wash, 100 μl NTA-AP was added to each well and the plate incubated at room temperature for 1.5 hours. After this time the fluid from each well was removed and discarded and each well was washed three times with 280 μl Tween/PBS. Next, 100 μl phosphatase substrate in PNPP buffer was added and the plate left for 1–2 hours at 30° C. The optical density of each well was measured at 405 nm.

Compounds were tested at a final concentration between 0 and 100 μM. Stock solutions of compound were made at 30 μM in DMSO, dilutions were made in $H_2O$.

Although the pharmacological properties of the compounds of the Formula (1) vary with structural change as expected, in general compounds of the Formula (1) possess an $IC_{50}$ in the above test in the range, for example, 0.03 to 200 μM. Thus by way of example the compound of Example 9 herein has an $IC_{50}$ of approximately 4 μM.

The invention will now be illustrated by the following non-limiting Examples in which, unless otherwise stated:

(i) concentrations and evaporations were carried out by rotary evaporation in vacuo;

(ii) operations were carried out at room temperature, that is in the range 18–26° C.;

(iii) yields, when given, are intended for the assistance of the reader only and are not necessarily the maximum attainable by diligent process development;

(iv) the following abbreviations are used:

BOC=tert-butoxycarbonyl; Cha=is an amino acid residue with a cyclohexylmethyl side chain; Dab=is an amino acid residue with a 2-aminoethyl side chain; DBU=1,8-diazabicyclo[5.4.0]undec-7-ene; DMF=N,N-dimethylformamide; HOBt=1-hydroxybenzotriazole; Met=methionine; Fmoc=9-fluorenylmethyloxycarbonyl; THF=tetrahydrofuran; DMSO=dimethylsulfoxide; HATU=O-(7-azabenzotriazol-1-yl)-1,1,3,3-tetramethyluronium hexafluorophosphate; HBTU=2-(1H-benzotriazol-1yl)-1,1,3,3-tetramethyluroniumhexafluorophosphate; HOAT=1-hydroxy-7-azabenzotriazole; DIPEA=diisopropylethylamine; TFA=trifluoroacetic acid; HPLC=high pressure liquid chromatography; TCE=trichloroethane; RP-HPLC=reverse phase high pressure liquid chromatography (which unless otherwise stated was carried out on a Vydac C18 column 218TP54, 4.6×250 mm); and Z=benzyloxycarbonyl;

(v) flash chromatography and chromatography on silica were performed on Merck Kieselgel 60 (Art No. 9385) obtained from E Merck, Darmstadt, Germany; and (vi) $^1H$ NMR spectra were determined at 200 Mhz in $CDCL_3$ or $d_6$-dimethylsulphoxide ($d_6$-DMSO) using tetramethylsilane (TMS) as an internal standard, and are expressed as chemical shift (delta) values in parts per million relative to TMS using conventional abbreviations for designation of major peaks: s, singlet; m, multiplet; t, triplet; br, broad, d, doublet.

EXAMPLE 1

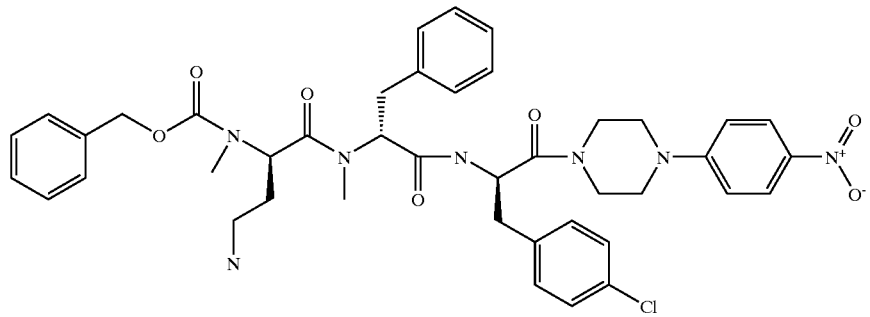

Z-NMe(D)Dab-NMe(D)Phe-(D)Phe(4-Cl)-piperazine-4-nitrophenyl

Z-NMe(D)Dab(BOC)-NMe(D)Phe-(D)Phe(4-Cl)-OH (assuming 0.25 mmol) was dissolved in DMF(1 ml). 4-Nitrophenyl-piperazine (1.2 eq, 1.5 mg). HATU(1 eq, 19 mg) and DIPEA(3.6 eq. 157 μl) were added and the mixture was stirred overnight at ambient temperature. RP-HPLC indicated that the reaction was 50% complete. It was evaporated to dryness and the BOC group removed by treatment with TFA/TIPS/water 10:1:1 (6 ml, 5:0.5:0.5).

The resulting peptide was purified by preparative RP-HPLC (Vydac C18 218TP1022 column eluting with an acetonitrile-water system containing 0.1% TFA (5 to 60% acetonitrile over 80 minutes), flow rate 12 ml/min). The fractions containing the product were combined and lyophilised to give Z-NMe(D)Dab-NMe(D)Phe-(D)Phe(4-Cl)-piperazine-4-nitrophenyl, 6.5 mg(3.25% yield).

The product was characterised by HPLC and mass spectrometry:

RP-HPLC Vydac C18 218TP54 4.6×250 mm column eluting at 1.2 ml/min in water and acetonitrile containing 0.1% TFA (30–70% acetonitrile over 20 minutes) retention time 15.27 minutes, no detectable impurities, mass spectrometry, m/e (positive electrospray, (ES+)) 798.5, 799.1, 800.5 (MH+).

The starting material was prepared by solid phase synthesis starting with Wang Resin in a Bond Elut (Varian 25 ml, fitted with a filter in the bottom):

Wang Resin(Novabiochem,1.28 g) was stirred in dichloromethane (15 ml)with MSNT (ref. Birgt Blankeymeyer-Menge, *Tet. Lett.* 1990, 31, 1701)(2 mmol, 592 mg) and Fmoc-Phe(4-Cl)-OH (2 mmol, 845 mg) for 45 minutes. The resin was washed with dichloromethane (3×10 ml) then methanol (3×10 ml). The resin was dried in vacuo at 40° C. overnight. Weight gain indicated a loading of 0.59 mmol/g for Fmoc(D)Phe(4-Cl)-Wang Resin.

The Fmoc group was removed with 20% piperidine in DMF (3×10 min, 10 ml each time) to give H-(D)Phe(4-Cl)-Wang Resin.

H-(D)Phe(4-Cl)-Wang Resin (423 mg~0.25 mmol) was placed in another Bond Elut (15 ml). FmocNMe(D)Phe-OH(3 eq, 301 mg) was dissolved in DMF(1.5 ml), HBTU (3 eq, 284 mg) and DIPEA (9 eq) were added. After 5 minutes this mixture was added to the resin and stirred for 1–1.5 h at ambient temperature. The resin was then washed with DMF (3×10 ml).

The Fmoc group was removed with 20% piperidine in DMF (3×10 min, 10 ml each time) to give NMe(D)Phe-(D)Phe(4-Cl)-Wang Resin.

Fmoc-Dab(BOC)-OH (3 eq, 340 mg) was coupled to the N-terminus of NMe(D)Phe(D)-Phe(4-Cl)-Wang Resin using a similar method to the coupling of Fmoc-Phe(4-Cl)-OH, except HATU(3 eq, 285 mg) was used instead of HBTU, to give Fmoc-Dab(BOC)NMe(D)Phe-(D)Phe(4-Cl)-Wang Resin.

The Fmoc group was removed with 20% piperidine in DMF (3×10 min, 10 ml each time) to give Dab(BOC)-NMe(D)Phe-(D)Phe(4-Cl)-Wang Resin.

The resin was washed with DMF(3×10 ml) and suspended in dichloromethane (5 ml) to which was added 2-nitrobenzenesulfonyl chloride (3 eq, 166 mg) and 2,4,6-collidine (5 eq, 165 μl). After 2 hours the resin was washed with dichloromethane (3×5 ml) and suspended in DMF (5 ml). To this was added MTBD (ref. Miller, *J. Am. Chem. Soc.*, 1997, 119,2301)(2–4 eq, 100 μl) and methyl-4-nitrobenzene sulfonate (3–5 eq, 200 mg). After 30 minutes the resin was washed with DMF (3×5 ml) and the resin suspended in DMF (5 ml). DBU (5 eq, 187 μl) and mercaptoethanol (10 eq, 175 μl) were added and after 30 minutes the resin was washed with DMF (5×10 ml).

The resin was wet with DMF (1–2 ml) and benzoyl chloroformate (4 eq, 170 mg) and DIPEA (12 eq, 0.52 ml) added. After 1.5 hours the resin was washed with DMF (3×10 ml) and then methanol (3×10 ml). The resin was dried once more in vacuo overnight to give Z-NMe-(D)Dab-NMe(D)Phe-(D)Phe(4-Cl)-Wang resin.

Z-NMeDab-NMe(D)Phe-(D)Phe(4-Cl)-OH was cleaved from the resin by addition of TFA:TIPS:water (10:1:1, 12 ml). The resin was filtered and washed thoroughly with TFA(3×5 ml) and the solution was evaporated to dryness and lyopholised from water to yield an oil.

The BOC group was reintroduced on to Z-NMeDab-NMe(D)Phe-(D)Phe(4-Cl)-OH (assuming 0.25 mmol) by treating it with di t-butyl-dicarbonate(4 eq) in DMF (1–2 ml) and DIPEA(12 ml). RP-HPLC indicated that the reaction was complete after 1 h (Vydac C18 218TP54 4.6×250 mm acetonitrile-water system containing 0.1% TFA, 10–90% acetonitrile over 20 minutes, flow 1.2 ml/min). The solution was evaporated to dryness and washed with 1M Citric acid (2×5 ml) then hexane(2×5 ml). It was dried in vacuo overnight in the presence of phosphorous pentoxide to give Z-NMe(D)Dab(BOC)-NMe(D)Phe-(D)Phe(4-Cl)-OH as an oil.

EXAMPLE 2

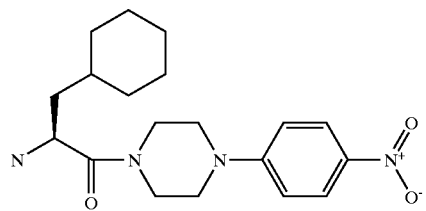

Cyclohexylalanine-piperazine-4-nitrophenyl

Fmoc-cyclohexylalanine (39 mg, 0.1 mmol) was dissolved in DMF (1 ml) and piperazine-4-nitrobenzene (25 mg, 1.2 eq), HATU (1.2 eq, 47 mg) and DIPEA (3.6 eq, 63 μl) were added and the mixture was stirred at ambient temperature.

The reaction was complete by RP-HPLC after 2 hours (Vydac C18 218TP54 4.6×250 mm column, water-acetonitrile system containing 0.1% TFA 10–90% gradient over 20 minutes, flow rate 1.2 ml/min) giving Fmoc-cyclohexylalanine-piperazine-4-nitrobenze. The protecting group was removed with 20% piperidine in DMF(2 ml) for 20 minutes. It was then diluted with water (5 ml). The amino acid amide was purified by preparative RP-HPLC Vydac 218TP1022 column flow rate 12 ml/min in a water-acetonitrile system containing 0.1% TFA using a 10–50% acetonitrile gradient over 1 hour.

Fractions containg product were combined and lyopholised to yield cyclohexylalanine-piperazine-4-nitrobenzene (36 mg, quantitative yield).

The product was characterised by HPLC, mass spectrometry and 1H NMR:

RP-HPLC Vydac C18 218TP54 column 4.6×250 mm eluting with acetonitrile and water containing 0.1% TFA, using a 10–50% acetonitrile gradient over 20 minutes, flow rate 1.2 ml/min, retention time 17.61 minutes with no detectable impurities.

Mass Spectrometry m/e (Electrospray(ES+)) 361.5 MH+

$^1$H-NMR(DMSO): 1.2 (m, 3H), 1.6 (m, 8H), 3.6 (m, 10H), 4.4 (m, 1H) 7.0 (d, 2H), 8.1 (m, 4H).

EXAMPLE 3

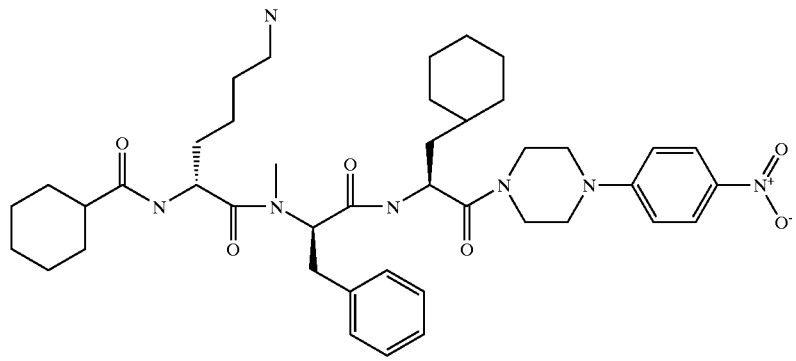

Cyclohexyl-CO-(D)Lys-NMe(D)Phe-Cha-piperazine-4-nitrophenyl

Cyclohexyl-CO-(D)Lys(BOC)-NMe(D)Phe-Cha-resin (0.05 mmol) was dissolved in DMF (1 ml) and activated with HATU (1 eq, 19 mg), DIPEA (3 eq, 26 μl) and coupled to N-(4-nitrophenyl)piperazine (1.5 eq, 15.5 mg) overnight. RP-HPLC indicated that the reaction was complete (VYDAC 201HS54 column, flow rate 1.2 ml/min water-acetonitrile gradient containing 0.1% TFA using a 10–90% acetonitrile gradient over 20 minutes).

The solution was evaporated to dryness and treated with a mixture of TFA/TIPS/water (12 ml, 10:1:1) for 30 minutes. After further evaporation to dryness the product was taken up in 50% acetonitrile/water and purified by preparative RP-HPLC (Dynamax 83–221 C 60 Angstrom column 12 ml/min in a water-acetonitrile system containing 0.1% TFA, using a 30–70% acetonitrile gradient over 1 hour. The fractions containing product were combined and lyonhilised to give cyclohexyl-CO-(D)Lys-MNe(D)Phe-Cha-piperazine-4-nitrobenzene.

The product was characterised by HPLC and mass spectrometry.

RP-HPLC Vydac C18 column, 218TP54, 4.6×250 mm eluting with water-acetonitrile containing 0.1% TFA, using a 20–60% acetonitrile gradient over 20 minutes, flow 1.2 ml/min indicates purity of 99.3%, retention time 15.11 minutes. Mass spectrometry m/e (Positive electrospray (ES+)) 759.7, 761, 761.9 (MH+).

The starting material was synthesised on an ABI 430 Automated Peptide Synthesiser starting from 2-chlorotritylchloride resin(Alexis, 188 mg, 0.25 mmol).

Fmoc Cha-OH (1 mmol each time) was double coupled to the chlorotrityl chloride resin in the standard way using, dichloromethane (5 ml each time) with diisopropylamine (2 eq, 348 μl each time) to give Fmoc-Cha-resin.

Fmoc was removed using a similar method to that used in example 1 but using 5 ml of piperidine in DMF each time.

Fmoc-NMe(D)Phe-OH (1 mmol, 401 mg) was coupled to Cha-resin using HBTU (1 mmol, 379 mg) and HOBT (1 mmol, 135 mg) in DMF with DIPEA (2 mmol, 378 μl), for 1 hour at ambient temperature. The resin was washed thoroughly with dichloromethane (5×5 ml) to give Fmoc-(D)NMe Ph-Cha-resin. Fmoc was removed using a similar method to that described in example 1.

Fmoc-Lys(BOC)-OH (1 mmol, 468 mg) was coupled to NMe(D)Ph-Cha-resin using HATU (1 mmol, 380 mg) in DMF with DIPEA (2 mmol, 348 μl), at ambient temperature for 1 hour. The resin was washed thoroughly with DMF (5×5 ml). Fmoc was removed using a similar method to that described in example 1.

Cyclohexanecarboxylic acid (1 mmol, 128 mg) was coupled to the peptide resin using a similar method to that used for the incorporation of Fmoc-NMe(D)Phe-OH. The peptide was cleaved from the resin using a mixture of acetic acid, trichloroethane and dichloromethane(14 ml 2:2:10) for 2 h. The resin was filtered and washed thoroughly with acetic acid:dichloromethane (1:4). The filtrate was evaporated to dryness and taken up in water and finally lyophilised to give cyclohexyl-CO-(D)Lys-(BOC)NMe(D)Phe-Cha-resin.

EXAMPLE 4

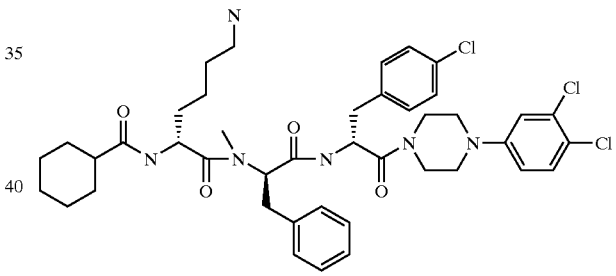

Cyclohexyl-(D)LysNMe(D)Phe-(D)Phe(4-Cl)-piperazine-3,4-dichlorophenyl

HATU (39 mg, 0.1 mmol) was added to a stirred solution of cyclohexyl-(D)Lys(BOC)-NMe(D)Phe(4-Cl)-OH (70 mg, 0.1 mmol), diisopropylethylamine (70 μl, 4 equivalents) and dichlorophenyl piperazine (24 mg, 0.1 mmol) in DMF (4 ml). After 1 hour at ambient temperature, RP-HPLC indicated that most of the acid had been consumed and a new peak, retention time 30.58 minutes (column and gradient as described at the bottom of this example) had been formed. The solvent was evaporated in vacuo, and the residue was dissolved in a mixture of TFA (9 ml), water (1 ml) and triethylsilane (0.3 ml). After 1 hour at ambient temperature, excess reagents were evaporated and the crude product now dissolved in acetonitrile (2 ml) and water (2 ml) for analytical and preparative RP-HPLC. The crude product was purified using preparative RP-HPLC (Dynamax C18, 1 inch internal diameter), using a gradient of acetonitrile-water containing 0.1% TFA (20–90% acetonitrile) over 60 minutes at a flow-rate of 12 ml/minute. Fractions which contained the title product (eluting at 50 minutes) were combined and freeze-dried. Yield 69.6 mg.

The product was characterised by HPLC, mass spectroscopy and amino-acid analysis.

RP-HPLC Vydac C18 column, 201HS54, 4.6×250 mm, eluting with acetonitrile and water containing 0.1% TFA, using a 20–60% acetonitrile gradient over 30 minutes, flow rate 1.2 ml/minute, retention time 22.15 minutes, no detectable impurities; mass spectrometry, m/e (positive electrospray (ES+)) 811.4 (MH+); amino acid analysis (acid hydrolysis over 24 hours using a solution of 6N HCl containing 1% phenol at 130° C.) gave Phe(4-Cl) 0.84, Lys 1.00.

The starting material was prepared as follows:

Fmoc-(D)Phe(4-Cl)-OH (844 mg, 2 mmol) was coupled to 2-chlorotritylchloride resin (Alexis, 0.75 g, 1 mmol) in the presence of diisopropylethylamine (2 mmol 0.35 ml) in DMF (8 ml) by an automated procedure on an Applied Biosystems 430A peptide synthesiser. After 1 hour at ambient temperature, the resin was filtered and washed with DMF. After deprotection with 20% piperidine in DMF (two treatments with 15 ml), the resin was thoroughly washed with DMF (5×10 ml). Fmoc-NMe(D)Phe-OH (803 mg, 2 mmol) was coupled to the resin-bound H-(D)Phe(4-Cl) by the standard HBTU/HOBt chemistry similar to that used in example 3. After extensive washing with DMF, the deprotection procedure described above was repeated to give H-NMe(D)Phe-(D)Phe(4-Cl)-resin. Fmoc-(D)Lys(BOC)-OH (938 mg, 2 mmol) was coupled by the HATU procedure (see J Chem Soc. Chem Comm. 1994, 201). After 1 hour at ambient temperature the resin as filtered and washed with DMF. After deprotection and extensive washing with DMF, cyclohexane carboxylic acid (256 mg, 2 mmol) was coupled by standard HBTU/HOBt chemistry similar to that described above to the resin bound tripeptide to give cyclohexyl-(D)Lys(BOC)-NMe(D)Phe-(D)Phe(4-Cl) on the resin. The peptide resin was collected and washed with methanol and dried, in vacuo, at 50° C. Yield 1.337 g (gain 587 mg).

The peptide was cleaved from the resin using a mixture of dichloromethane (20 ml), trifluoroethanol (4 ml) and acetic acid (4 ml) at ambient temperature. After 2 hours, the mixture was filtered and the resin was washed with a mixture of acetic acid in dichloromethane (5%) (5×20 ml). The combined filtrate and washes were evaporated to dryness and the residue was dissolved in a mixture of acetonitrile (100 ml) and water (50 ml) for analytical RP-HPLC and lyophilisation. Yield 604 mg (86%).

RP-HPLC Vydac C18 column, 201HS54, 4.6×250 mm, eluting with acetonitrile and water containing 0.1% TFA, using a 20–80% acetonitrile gradient over 40 minutes, flow rate 1.2 ml/minute, indicated 100% purity, retention time 22.05 minutes no detectable impurities.

EXAMPLE 5

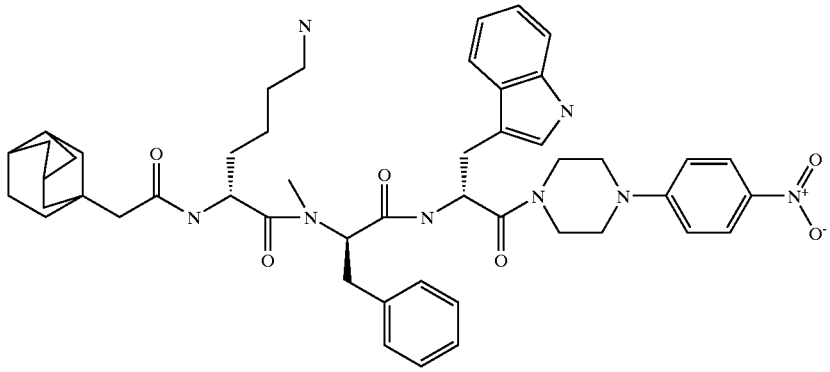

Adamantylacetyl-(D)Lys-NMe(D)Phe-(D)Trp-piperazine-4-nitrophenyl

Adamantylacetyl-(D)Lys(BOC)-NMe(D)Phe-(D)Trp-OH (77 mg, 0.1 mmol) was coupled to 4-(nitrophenzyl)piperazine (21 mg, 0.1 mmol) by a similar procedure to that described in example 4. Analytical RP-HPLC (column and conditions as for the protected peptide acid below) indicated almost complete conversion to the amide, retention time 23.39 minutes. After deprotection with TFA and scavengers (water and triisopropylsilane), the crude product was purified by preparative RP-HPLC (Dynamax C18, 1 inch internal diameter using a gradient of acetonitrile-water containing 0.1% TFA (20–70% acetonitrile) over 60 minutes at a flow rate of 12 ml/minute. Fractions which contained the pure title product (eluting at 55 minutes) were combined and freeze dried. Yield 43 mg.

The product was characterised by HPLC and mass spectroscopy. RP-HPLC (column and conditions exactly as for previous example) indicated 100% purity, retention time 19.66 minutes; mass spectrometry m/e (positive electrospray (ES+)) 859.6 (MH+).

The starting material was prepared as follows:

Adamantylacetyl-(D)Lys(BOC)-NMe(D)Phe-(D)Trp-OH was prepared by a similar method to that described in example 4, but on a smaller scale (0.4 mmol). Yield 186 mg (60%).

RP-HPLC Vydac C18 column, 201HS54, 4.6×250 mm, eluting with acetonitrile and water containing 0.1% TFA, using a 25–90% acetonitrile gradient over 40 minutes, flow rate 1.2 ml/minute, retention time 19.24 minutes, no detectable impurities.

EXAMPLE 6

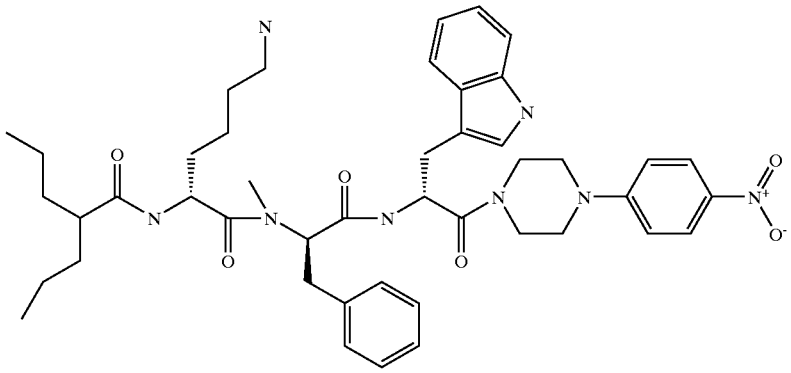

2-Propylpentanoyl-(D)Lys-NMe(D)Phe-(D)Trp-piperazine-4-nitrophenyl

This title compound was prepared using a similar method to that of example 4. The protected peptide amide had a retention time of 22 minutes on RP-HPLC (column and conditions as for the protected peptide acid below). After deprotection with TFA and scavengers, preparative RP-HPLC was performed exactly as described for the proceeding example and fractions which contained product (eluting at 40 minutes) were combined and freeze dried. Yield 93 mg.

RP-HPLC (column and conditions as for the previous example) retention time 17.92 minutes; mass spectroscopy, m/e (positive electrospray (ES$^+$) 809.6 (MH$^+$).

The starting material was prepared as follows:

2-Propylpentanoyl-(D)Lys(BOC)-NMe(D)Phe-DTrp-OH was prepared by the same method as described in example 4, but on a smaller scale (0.33 mmol). Yield 248 mg (82%). RP-HPLC Vydac C18 column 201HS54, 4.6×250 mm, eluting with acetonitrile and water containing 0.1% TFA, using a 25–90% acetonitrile gradient over 40 minutes, flow rate 1.2 ml/minute, retention time 18 minutes, no detectable impurities.

EXAMPLE 7

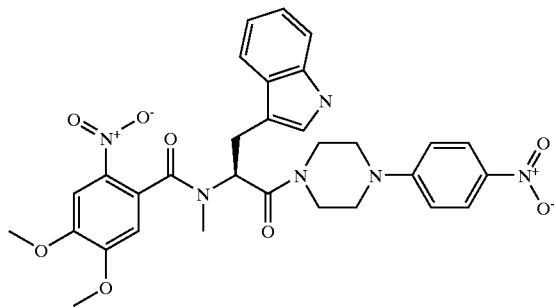

4,5-Dimethoxy-2-nitrobenzoyl-NMeTrp-piperazine-4-nitrophenyl

A portion of 4,5-dimethoxy-2-nitrobenzoyl-NMeTrp-OH (43 mg, 0.1 mmol) was coupled to 4-(nitrophenyl)piperazine (21 mg, 0.1 mmol) in DMF (4 ml) using diisopropylethylamine (80 microliters, 4 equivalents) and HATU (38 mg, 1 mmol). The reaction was complete after 1 hour, as judged by HPLC. The solution was diluted with water (2 ml), filtered and put directly on a Dynamax C18 preparative column and eluted with a gradient of acetonitrile-water containing 0.1% TFA (20–70% acetonitrile) over 70 minutes at a flow rate of 12 ml/minute. Fractions which contained product (eluting at 65 minutes) were combined and freeze dried. Yield 32 mg.

RP-HPLC retention time 19.83 minutes (column and conditions as for previous example); mass spectroscopy, m/e (negative electrospray (ES$^-$)) 615.4 (MH$^-$).

The starting material was prepared as follows:

4,5-Dimethoxy-2-nitrobenzoyl-NMeTrp-OH was prepared from 2-chlorotritylchloride resin (Alexis, 380 mg, 0.5 mmol) by the automated procedure described in example 4. After coupling Fmoc-NMeTrp-OH to the resin and subsequent Fmoc-deprotection, 4,5-dimethoxy-2-nitrobenzoic acid was coupled to the resin-bound NMethyl-Trp by the HATU procedure. The completed resin was collected and washed with methanol and dried at 50°. Yield 487 mg (gain 107 mg).

The 4,5-dimethoxy-2-nitrobenzoyl-NMeTrp-OH was cleaved from the resin with dichloromethane, trifluoroethanol and acetic acid as described previously. It was freeze-dried from water and acetonitrile. Yield 173 mg (yellow powder) (82%) RP-HPLC at 50° C., Vydac C18, 201HS54 column, 4.6×250 mm, eluting with a gradient of 5–50% acetonitrile, 0.1% TFA acetonitrile-water over 40 minutes, flow rate 1.3 ml/minute, retention time 17.26 minutes, mass spectroscopy, m/e (negative electrospray (ES$^-$)) 425.6 (MH$^-$).

EXAMPLE 8

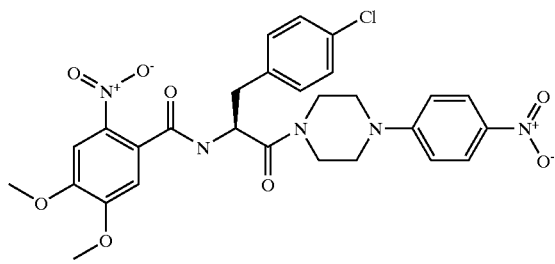

4,5Dimethoxy-2-nitrobenzoyl-Phe(4-Cl)-piperazine-4-nitrophenyl

This was prepared using a similar method to that of example 7. Preparative RP-HPLC was performed using a gradient 20–80% acetonitrile, 0.1% TFA over 70 minutes. Fractions which contained the title product (eluting at 59 minutes) were pooled and freeze-dried. Yield 40 mg.

RP-HPLC column and element as for previous example, except that gradient 10–70% acetonitrile over 30 minutes, retention time 20.81 minutes; mass spectroscopy, m/e (negative electrospray (ES$^-$) 596.3 (MH$^-$).

The starting material was prepared as follows:

4,5-Dimethoxy-2-nitrobenzoyl-Phe(4-Cl)-OH was prepared using a similar method to that of example 7. Yield 203 mg (100%).

RP-HPLC Vydac C18 column, 201HS54 4.6×250 mm, eluting with a gradient 10–70%, 0.1% TFA acetonitrile-water over 40 minutes, flow rate 1.2 ml/minue, retention time 178.5 minutes.

EXAMPLE 9

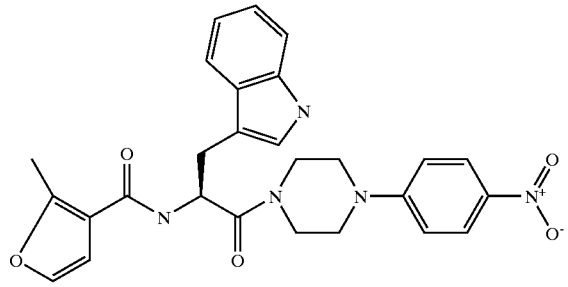

2-Methyl-3-furoyl-Trp-piperazine-4-nitrophenyl

The amminolysis of 2-methyl-3-furoyl-Trp-O-Kaiser's oxime resin was carried out at 80° C. in trichloroethane for 2 hours with 1 equivalent of 4-nitrophenylpiperazine and acetic acid (1–2 molar). The mixture was filtered and the resin was washed repeatedly with dichloromethane. The combined filtrate and washings were evaporated to dryness and the residue was dissolved in water (4 ml) and acetonitrile (4 ml) for HPLC and LC-MS, then freeze dried. Yield 29.8 mg.

RP-HPLC column and elements as for previous examples, gradient 5–70%, 0.1% TFA acetonitrile-water over 40 minutes, flow 1.2 ml/minute. Indicated that main peak (retention time 25.5 minutes) was expected product, (65.7% by peak integration at 230 nm). LC MS MH$^+$ for main peak 502.3 (calc 501.55 mw).

The starting material was prepared as follows:

BOC-Trp-OH (4.6 g, 15 mmol) was dissolved in dichloromethane (30 ml) containing DMF (3 ml) and diisopropylcarbodiimide (0.95 g, 7.5 mmol) was added. After 20 minutes at ambient temperature, the solution of preformed symmetrical anhydride was added to a bond-elute tube (80 ml) containing Kaiser's oxime resin (5 g, 1.21 mmol/g, 6 mmol), which was already swollen in dichloromethane. After manual mixing for 5 minutes, dimethylamino pyridine (92 mg, 0.75 mmol) was added and mixing continued at intervals over 2 hours. The resin was filtered and washed repeatedly with dichloromethane. Unreacted sites on the resin were then "capped" with 2,6-dichlorobenzoylchloride (0.63 g, 3 mmol) in dichloromethane (30 ml). After 1 hour at ambient temperature, the resin was filtered and washed with dichloromethane.

Deprotection was performed with 25% TFA in dichloromethane containing triisopropylsilane (5%). Three separate treatments carried out for 10 minutes each to ensure complete removal of BOC group. After extensive washing with dichloromethane to ensure most of the surplus TFA had been removed, the resin was divided into roughly equal portions, into 50 bond elute tubes (3 ml) to give 0.12 mmol of TFA salt of Trp-O-oxime resin per tube.

To one of these portions of loaded resin, was added 2-methyl-3-furoic acid (64 mg, 0.5 mmol) dissolved in a solution of HBTU in DMF (0.33M, 1.5 ml, 1 equivalent), followed after brief mixing, by isopropylethylamine (263 microliter, 1.5 mmol). After 5 hours at ambient temperature, the resin was filtered and washed with DMF to afford 2-methyl-3-furoyl-Trp-O-oxime resin.

EXAMPLE 10

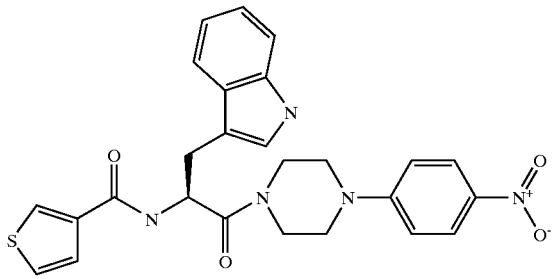

Thien-3-ylcarbonyl-Trp-piperazine-4-nitrophenyl

The title compound was prepared by substitution of thiophene-3-carboxylic acid for the furoic acid in example 9, and the title compound was obtained by freeze drying. Yield 41 mg.

RP-HPLC column and conditions as described in the previous example. Retention time 24.78 minutes, 77% by peak integration at 230 nm. LC MS M+H$^+$ for main peak 504.2.

EXAMPLE 11

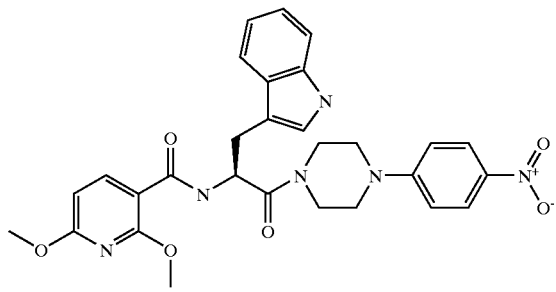

2,6-Dimethoxynicotinoyl-Trp-piperazine-4-nitrophenyl

The title compound was prepared by substitution of 2,6-dimethoxynicotinic acid for the furoic acid in example 9. Yield 39.5 mg.

RP-HPLC column and conditions as described in examples above.

Retention time 27.9 minutes, 78% by peak integration at 230 nm. LC MS MH$^+$ for main peak 559.6.

EXAMPLE 12

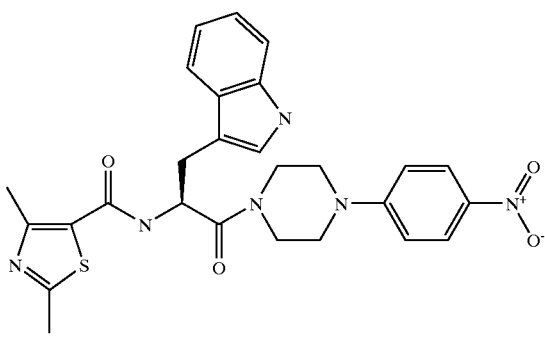

2,4-Dimethylthiazol-5-ylcarbonyl-(L)-Trp-4-piperazine-4-nitrophenyl

This preparation was performed as part of a run on the Abimed AMS432 multiple parallel peptide synthesiser (MPPS) synthesiser:

BOC-(L)-Trp-oxime resin (100 mg 110 μmol) (prepared as in example 9) was placed in a reactor (8 ml Bond-Elut). The instrument had been programmed to swell the resin by rinsing with dichloromethane. The resin was next treated 4×10 minutes with 25% TFA in dichloromethane which removes the BOC group. The resin was rinsed 6 times for 1 minute with dichloromethane, followed by 6 rinses for 1 minute with DMF. 2,4-Dimethylthiazole-5-carboxylic acid DIPEA (1000 μl of 0.5M) in NMP (1.0M) and HBTU in NMP (1100 μl 0.45M) were added to the resin. The mixture was stirred briefly by hand then allowed to proceed for 1 hour. The reaction mixture was drained and the resin rinsed 6 times with DMF and 3 times with dichloromethane and allowed to air dry to give 2,4-dimethylthiazole-5-carbonyl-(L)-Trp-oxime resin.

The resin was transferred to a sealed reaction vessel and suspended in TCE (2 ml). The suspension was treated with 1 ml of a solution containing N-(4-nitrophenyl)-piperazine (100 μmol) and glacial acetic acid (400 μmol). The reaction vessel was sealed then left overnight in an oven at 75–80° C. After the overnight reaction, the reaction mixture was filtered, the residual resin was rinsed 4 times with DMSO (0.5 ml). The combined filtrates were evaporated to dryness on a centrifugal evaporator and the residue was re-dissolved in DMSO (5 ml ca 20 mM solution). The solution was stored frozen at −20° C.

A sample of the solution was diluted 50 times with water to provide a sample for LC-MS analysis:

Theory mH$^+$=533.6, Found mH$^+$=533.1.

---

What is claimed is:

1. A compound of formula (1):

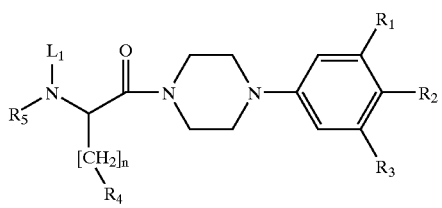

formula (1)

wherein:

$L_1$ is hydrogen or methyl;

$R_1$ and $R_2$ and $R_3$ are each independently hydrogen, halo, nitro, cyano, carbamoyl, N-($C_{1-4}$alkyl)carbamoyl, NN-(di$C_{1-4}$alkyl)carbamoyl or $C_{1-4}$alkoxycarbonyl;

$R_4$ is indole, N-($C_{1-4}$ alkyl) indole, $C_{5-7}$carbocyclic ring or aryl, any of which can be optionally substituted on ring carbon atoms with up to three substituents each independently selected from halo, $C_{1-4}$alkyl, or $C_{1-4}$alkoxy;

$R_5$ is hydrogen, $C_{1-4}$alkyl, $R_6CH_2$— or $R_6C(O)$—;

$R_6$ is aryl, heteroaryl, heterocyclyl, amino$C_{3-6}$alkyl, N-($C_{1-4}$alkyl)amino$C_{3-6}$alkyl, NN-(di$C_{1-4}$alkyl) amino$C_{3-6}$alkyl, or $R_7$; wherein the aryl, heteroaryl or heterocyclyl rings may be optionally substituted with up to three substituents independently selected from nitro, $C_{1-4}$alkyl, $C_{1-4}$alkoxy, halo, ($C_{1-4}$alkyl)sulfanyl, N-($C_{1-4}$ alkyl)carbamoyl, NN-(di$C_{1-4}$ alkyl)carbamoyl, N-($C_{1-4}$ alkyl)amino or NN-(di$C_{1-4}$ alkyl)amino;

wherein $R_7$ is either a group of formula (2) or of formula (3):

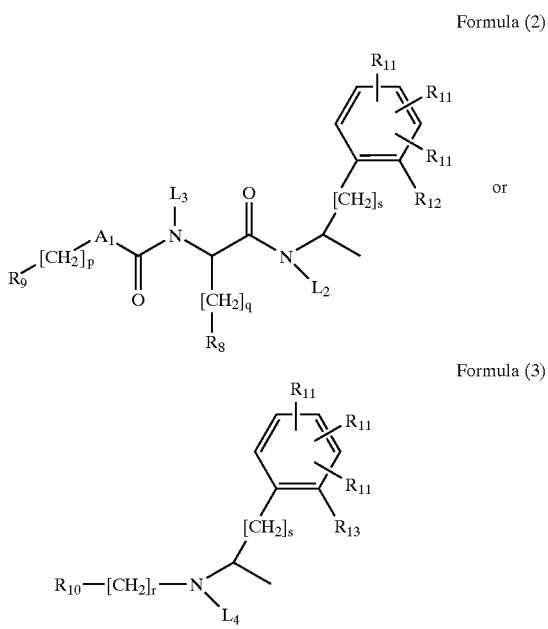

Formula (2)

Formula (3)

wherein:

$L_2$, $L_3$ and $L_4$ are each independently hydrogen or methyl;

$R_8$ is amino, guanadino or, imidazolo, any of which can be mono or di-N-substituted with $C_{1-4}$alkyl;

$A_1$ is oxygen or a direct bond;

$R_9$ is a $C_{5-8}$ membered mono-carbocyclic ring, a $C_{6-10}$ membered bi-carbocyclic ring, $C_{8-12}$ membered tri-carbocyclic ring, $C_{5-7}$alkyl or aryl, any of which can be optionally mono, bi or tri substituted by $C_{1-4}$ alkyl;

$R_{10}$ is $C_{1-6}$alkyl or a $C_{3-8}$mono-carbocyclic ring;

$R_{11}$ is hydrogen, halo, $C_{1-4}$alkyl, or $C_{1-4}$alkoxy;

$R_{12}$ is hydrogen or methyl or ethyl or $R_{12}$ together with $L_2$ forms a $C_{5-7}$ nitrogen-containing heterocyclic ring;

$R_{13}$ is hydrogen or methyl or ethyl or $R_{13}$ together with $L_4$ forms a $C_{5-7}$ nitrogen-containing heterocyclic ring;

n is 0, 1 or 2;

p is 0, 1 or 2;

q is an integer from 1 to 6;

r is 0, 1 or 2;

s is 0, 1 or 2;

provided that when $R_6$ is aryl, heteroaryl, heterocyclyl, amino$C_{3-6}$alkyl, N-($C_{1-4}$alkyl)amino$C_{3-6}$alkyl or NN-(di$C_{1-4}$alkyl)amino$C_{3-6}$alkyl then $R_5$ is other than $R_6CH_2$—; and when $R_1$ to $R_3$ are each hydrogen, $L_1$ is hydrogen, n is 1, $R_4$ is phenyl, $R_5$ is $R_6C(O)$—, then $R_6$ cannot be 2-methyl-4-amino-butyl, and excluding (S)-4-chloro-N-[1-(1H-indol-3-ylmethyl)-2-oxo-2-(4-phenyl-1-piperazinyl)ethyl]-N-methyl-benzamide;

or a pharmaceutically acceptable salt, prodrug or solvate thereof.

2. A compound according to claim 1 wherein $R_5$ is hydrogen.

3. A compound according to claim 2 wherein $R_1$ is hydrogen; $R_2$ is nitro; $R_3$ is hydrogen; n is 1; $R_4$ is indole, N-($C_{1-4}$ alkyl)indole, cyclohexyl or phenyl any of which can be optionally substituted on ring carbon atoms with up to three substituents each independently selected from halo, $C_{1-4}$alkyl, or $C_{1-4}$alkoxy, $L_1$ is hydrogen and $R_5$ is hydrogen.

4. A compound according to claim 1 wherein $R_5$ is $R_6C(O)$—; $R_6$ is aryl, heteroaryl, heterocyclyl, amino$C_{3-6}$alkyl, N-($C_{1-4}$alkyl)amino$C_{3-6}$alkyl, or NN-(di$C_{1-4}$alkyl) amino$C_{3-6}$alkyl, wherein the aryl, heteroaryl or heterocyclyl rings can be optionally substituted on ring carbon atoms with up to three substituents each independently selected from nitro, halo, $C_{1-4}$alkyl, or $C_{1-4}$alkoxy.

5. A compound according to claim 4 wherein $R_1$ is hydrogen; $R_2$ is nitro; $R_3$ is hydrogen; n is 1; $L_1$ is hydrogen; and $R_6$ is aryl or heteroaryl wherein the aryl or heteroaryl can be optionally substituted on ring carbon atoms with up to three substituents each independently selected from nitro, halo, $C_{1-4}$alkyl, or $C_{1-4}$alkoxy.

6. A compound according to claim 1 wherein $R_6$ is $R_7$.

7. A compound according to claim 6 wherein $R_7$ is of Formula (2).

8. A compound according to claim 7 wherein $R_1$ is hydrogen; $R_2$ is nitro; $R_3$ is hydrogen; n is 1; $L_1$ is hydrogen; $L_2$ is hydrogen or methyl; q is an integer between 2 and 4; $R_8$ is amino; s is 1 and $L_3$ is hydrogen or methyl.

9. A compound according to claim 6 wherein $R_7$ is of Formula (3).

10. A compound according to claim 9 wherein $R_1$ is hydrogen; $R_2$ is nitro; $R_3$ is hydrogen; n is 1; s is 1 and $L_1$ is hydrogen.

11. A compound selected from the following:

4,5-dimethoxy-2-nitrobenzoyl-Phe(4-Cl)-piperazine-4-nitrophenyl;

4,5-dimethoxy-2-nitrobenzoyl-NMe-Trp-piperazine-4-nitrophenyl;

4,5-dimethoxy-2-nitrobenzoyl-(D)($N^{in}$-Me)Trp-piperazine-4-nitrophenyl;

Z-(D)(NMe)Dab-(NMe)(D)Phe-(D)Trp-piperazine-4-nitrophenyl;

Z-NMe(D)Lys-NMe(D)Phe-(D)Phe(4-Cl)-piperazine-4-nitrophenyl;

cyclohexyl-CO-(D)Lys-(D)NMe-Phe-Cha-piperazine-4-nitrophenyl;

cyclohexyl-(D)Lys-(D)(NMe)Phe-(D)Phe(4-Cl)-piperazine-4-nitrophenyl;

cyclohexyl-CH$_2$-(D,L)NMe-Phe{CH$_2$NH}(D)Trp-piperazine-4-nitrophenyl; and cyclohexyl-(D)Lys-(D)(NMe)Phe-(D)hPhe-piperazine-4-nitrophenyl;

or a pharmaceutically acceptable salt, prodrug or solvate thereof.

12. A pharmaceutical composition which comprises a compound according to claim 1 and a pharmaceutically acceptable carrier.

13. A method of treating cancer, comprising administering to a warm-blooded animal an effective amount of a compound of formula (4):

formula (4)

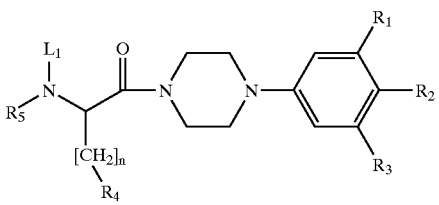

wherein:
L$_1$ is hydrogen or methyl;
R$_1$ and R$_2$ and R$_3$ are each independently hydrogen, halo, nitro, cyano, carbamoyl, N-(C$_{1-4}$alkyl)carbamoyl, NN-(diC$_{1-4}$alkyl)carbamoyl or C$_{1-4}$alkoxycarbonyl;
R$_4$ is indole, N-(C$_{1-4}$ alkyl) indole, C$_{5-7}$carbocyclic ring or aryl, any of which can be optionally substituted on ring carbon atoms with up to three substituents each independently selected from halo, C$_{1-4}$alkyl, or C$_{1-4}$alkoxy;
R$_5$ is hydrogen, C$_{1-4}$alkyl, R$_6$CH$_2$— or R$_6$C(O)—;
R$_6$ is aryl, heteroaryl, heterocyclyl, aminoC$_{3-6}$alkyl, N-(C$_{1-4}$alkyl)aminoC$_{3-6}$alkyl, NN-(diC$_{1-4}$alkyl)aminoC$_{3-6}$alkyl, or R$_7$; wherein the aryl, heteroaryl or heterocyclyl rings may be optionally substituted with up to three substituents independently selected from nitro, C$_{1-4}$alkyl, C$_{1-4}$alkoxy, halo, (C$_{1-4}$alkyl)sulfanyl, N-(C$_{1-4}$ alkyl)carbamoyl, NN-(diC$_{1-4}$ alkyl)carbamoyl, N-(C$_{1-4}$ alkyl)amino or NN-(diC$_{1-4}$ alkyl)amino;
wherein R$_7$ is either a group of formula (5) or of formula (6):

Formula (5)

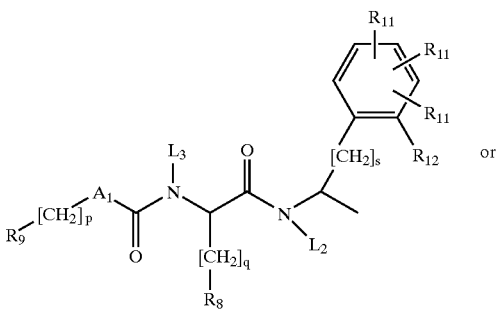

Formula (6)

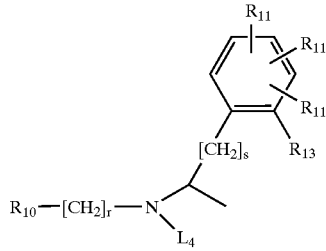

wherein:
L$_2$, L$_3$ and L$_4$ are each independently hydrogen or methyl;
R$_8$ is amino, guanadino or imidazolo, any of which can be mono or di-N-substituted with C$_{1-4}$alkyl;
A$_1$ is oxygen or a direct bond;
R$_9$ is a C$_{5-8}$ membered mono-carbocyclic ring, a C$_{6-10}$ membered bi-carbocyclic ring, C$_{8-12}$ membered tri-carbocyclic ring, C$_{5-7}$alkyl or aryl, any of which can be optionally mono, bi or tri substituted by C$_{1-4}$ alkyl;
R$_{10}$ is C$_{1-6}$alkyl or a C$_{3-8}$mono-carbocyclic ring;
R$_{11}$ is hydrogen, halo, C$_{1-4}$alkyl, or C$_{1-4}$alkoxy;
R$_{12}$ is hydrogen or methyl or ethyl or R$_{12}$ together with L$_2$ forms a C$_{5-7}$ nitrogen-containing heterocyclic ring;
R$_{13}$ is hydrogen or methyl or ethyl or R$_{13}$ together with L$_4$ forms a C$_{5-7}$ nitrogen-containing heterocyclic ring;
n is 0, 1 or 2;
p is 0, 1 or 2;
q is an integer from 1 to 6,
r is 0, 1 or 2;
s is 0, 1 or 2;
provided that when R$_6$ is aryl, heteroaryl, heterocyclyl, aminoC$_{3-6}$alkyl, N-(C$_{1-4}$alkyl)aminoC$_{3-6}$alkyl or NN-(diC$_{1-4}$alkyl)aminoC$_{3-6}$alkyl then R$_5$ is other than R$_6$CH$_2$; or a pharmaceutically acceptable salt, prodrug or solvate thereof.

14. A compound of formula (1a):

formula (1a)

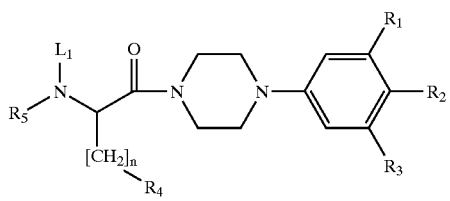

wherein:
L$_1$ is hydrogen or methyl;
R$_1$ and R$_2$ and R$_3$ are each independently hydrogen, halo, nitro, cyano, carbamoyl, N-(C$_{1-4}$alkyl)carbamoyl, NN-(diC$_{1-4}$alkyl)carbamoyl or C$_{1-4}$alkoxycarbonyl;
R$_4$ is indole, N-(C$_{1-4}$ alkyl) indole, C$_{5-7}$carbocyclic ring or aryl, any of which can be optionally substituted on ring carbon atoms with up to three substituents each independently selected from halo, C$_{1-4}$alkyl, or C$_{1-4}$alkoxy;
R$_5$ is hydrogen, C$_{1-4}$alkyl, R$_6$CH$_2$— or R$_6$C(O)—;
R$_6$ is aryl, heteroaryl, heterocyclyl, aminoC$_{3-6}$alkyl, N-(C$_{1-4}$alkyl)aminoC$_{3-6}$alkyl, NN-(diC$_{1-4}$alkyl)

aminoC$_{3-6}$alkyl, or R$_7$; wherein the aryl, heteroaryl or heterocyclyl rings may be optionally substituted with up to three substituents independently selected from nitro, C$_{1-4}$alkyl, C$_{1-4}$alkoxy, (C$_{1-4}$alkyl)sulfanyl, N-(C$_{1-4}$ alkyl)carbamoyl, NN-(diC$_{1-4}$ alkyl)carbamoyl, N-(C$_{1-4}$ alkyl)amino or NN-(diC$_{1-4}$ alkyl)amino;

wherein R$_7$ is either a group of formula (2) or of formula (3):

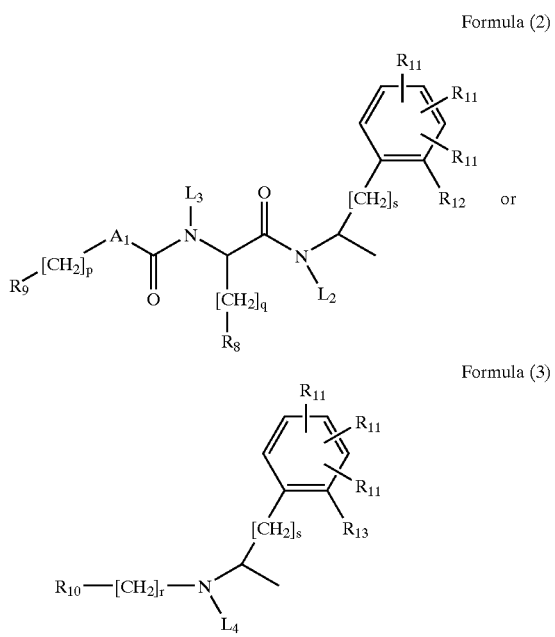

Formula (2)

Formula (3)

wherein:

L$_2$, L$_3$ and L$_4$ are each independently hydrogen or methyl;

R$_8$ is amino, guanadino or imidazolo, any of which can be mono or di-N-substituted with C$_{1-4}$alkyl;

A$_1$ is oxygen or a direct bond;

R$_9$ is a C$_{5-8}$ membered mono-carbocyclic ring, a C$_{6-10}$ membered bi-carbocyclic ring, C$_{8-12}$ membered tri-carbocyclic ring, C$_{5-7}$alkyl or aryl, any of which can be optionally mono, bi or tri substituted by C$_{1-4}$ alkyl;

R$_{10}$ is C$_{1-6}$alkyl or a C$_{3-8}$mono-carbocyclic ring;

R$_{11}$ is hydrogen, halo, C$_{1-4}$alkyl, or C$_{1-4}$alkoxy;

R$_{12}$ is hydrogen or methyl or ethyl or R$_{12}$ together with L$_2$ forms a C$_{5-7}$ nitrogen-containing heterocyclic ring;

R$_{13}$ is hydrogen or methyl or ethyl or R$_{13}$ together with L$_4$ forms a C$_{5-7}$ nitrogen-containing heterocyclic ring;

n is 0, 1 or 2;

p is 0, 1 or 2;

q is an integer from 1 to 6;

r is 0, 1 or 2;

s is 0, 1 or 2;

provided that when R$_6$ is aryl, heteroaryl, heterocyclyl, aminoC$_{3-6}$alkyl, N-(C$_{1-4}$alkyl)aminoC$_{3-6}$alkyl or NN-(diC$_{1-4}$alkyl)aminoC$_{3-6}$alkyl then R$_5$ is other than R$_6$CH$_2$—; and when R$_1$ to R$_3$ are each hydrogen, L$_1$ is hydrogen, n is 1, R$_4$ is phenyl, R$_5$ is R$_6$C(O)—, then R$_6$ cannot be 2-methyl-4-amino-butyl, or a pharmaceutically acceptable salt, prodrug or solvate thereof.

15. A pharmaceutical composition comprising a compound of claim 1, or a compound of claim 14, or a pharmaceutically acceptable salt, prodrug or solvate thereof, in admixture with a pharmaceutically acceptable diluent or carrier.

* * * * *

UNITED STATES PATENT AND TRADEMARK OFFICE
CERTIFICATE OF CORRECTION

PATENT NO.    : 6,770,627 B1
DATED         : August 3, 2004
INVENTOR(S)   : Richard W. A. Luke et al.

It is certified that error appears in the above-identified patent and that said Letters Patent is hereby corrected as shown below:

Title page,
Item [75], Inventors, "Richard Wa Luke" should be -- Richard W. A. Luke --.

Column 1,
Lines 5-7, please delete "the national phase of international application PCT/GB99/02957 filed Sep. 7, 1999 which designated the U.S." and instead insert -- a national stage filing under 35 U.S.C. 371 of International Application PCT/GB99/02957, filed Sep. 7, 1999, which claims priority form United Kingdom Application No. 9819860.9, filed Sep. 12, 1998, the specifications of each of which are incorporated by reference herein. International Application PCT/GB99/02957 was published under PCT Article 21(2) in English. --.

Signed and Sealed this

First Day of February, 2005

JON W. DUDAS
*Director of the United States Patent and Trademark Office*